US006432707B1

(12) United States Patent
Reed et al.

(10) Patent No.: US 6,432,707 B1
(45) Date of Patent: Aug. 13, 2002

(54) COMPOSITIONS AND METHODS FOR THE THERAPY AND DIAGNOSIS OF BREAST CANCER

(75) Inventors: Steven G. Reed; Jiangchun Xu, both of Bellevue; Davin C. Dillon, Issaquah, all of WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/602,877

(22) Filed: Jun. 22, 2000

Related U.S. Application Data

(63) Continuation-in-part of application No. 09/346,327, filed on Jul. 2, 1999, which is a continuation-in-part of application No. 09/288,950, filed on Apr. 9, 1999, now abandoned, which is a continuation-in-part of application No. 09/248,178, filed on Feb. 9, 1999, which is a continuation-in-part of application No. 09/118,627, filed on Jul. 17, 1998, which is a continuation-in-part of application No. 08/998,253, filed on Dec. 24, 1997, now abandoned.

(51) Int. Cl.[7] .............................. C12H 5/02; C12N 1/20; C12N 15/00; C07H 17/00

(52) U.S. Cl. ................. 435/325; 435/252.3; 435/320.1; 536/23.1; 514/44

(58) Field of Search ...................... 536/23.1; 435/320.1, 435/325, 252.3, 69.1; 574/44

(56) References Cited

FOREIGN PATENT DOCUMENTS

| EP | 0679716 A | 11/1995 |
|---|---|---|
| WO | WO 94/21287 | 9/1994 |
| WO | WO 94/23728 | 10/1994 |
| WO | WO 95/11986 | 5/1995 |
| WO | WO 95/19783 | 7/1995 |
| WO | WO 97/02280 | 1/1997 |
| WO | WO 97/25426 | 7/1997 |
| WO | WO 97/34921 | 9/1997 |
| WO | WO 98/18945 | 5/1998 |
| WO | WO 99/33869 | 7/1999 |

OTHER PUBLICATIONS

Genbank Sequence Database, Accession No. AA124124, Feb. 17, 1997.
Genbank Sequence Database, Accession No. AA133706, Jul. 31, 1997.
Genbank Sequence Database, Accession No. AA150963, May 19, 1997.
Genbank Sequence Database, Accession No. AA163045, Feb. 16, 1997.
Genbank Sequence Database, Accession No. AA214632. Aug. 13, 1997.
Genbank Sequence Database, Accession No. AA243535, Aug. 15, 1997.
Genbank Sequence Database, Accession No. AA256631, Aug. 6, 1997.
Genbank Sequence Database, Accession No. AA258236, Aug. 13, 1997.
Genbank Sequence Database, Accession No. AA259166, Aug. 15, 1997.
Genbank Sequence Database, Accession No. AA299443, Apr. 18, 1997.
Genbank Sequence Database, Accession No. AA340069, Apr. 21, 1997.
Genbank Sequence Database, Accession No. AA364013, Apr. 21, 1997.
Genbank Sequence Database, Accession No. AA366358, Apr. 21, 1997.
Genbank Sequence Database, Accession No. AA413174, May 2, 1997.
Genbank Sequence Database, Accession No. AA425487, Oct. 16, 1997.
Genbank Sequence Database, Accession No. AA451680, Jun. 5, 1997.
Genbank Sequence Database, Accession No. AA456968, Jun. 6, 1997.
Genbank Sequence Database, Accession No. AA457077, Jun. 6, 1997.
Genbank Sequence Database, Accession No. AA478500, Aug. 8, 1997.
Genbank Sequence Database, Accession No. AA490863, Aug. 15, 1997.
Genbank Sequence Database, Accession No. AA535894, Aug. 21, 1997.
Genbank Sequence Database, Accession No. AA535981, Aug. 21, 1997.
Genbank Sequence Database, Accession No. AA552419, Sep. 5, 1997.
Genbank Sequence Database, Accession No. AA610465, Oct. 30, 1997.
Genbank Sequence Database, Accession No. AA613497, Oct. 30, 1997.
Genbank Sequence Database, Accession No. AA626243, Oct. 15, 1997.
Genbank Sequence Database, Accession No. AA646568, Oct. 28, 1997.
Genbank Sequence Database, Accession No. AA701126, Dec. 19, 1997.

(List continued on next page.)

Primary Examiner—Karen Cochrane Carlson
(74) Attorney, Agent, or Firm—Seed Intellectual Property Law Group PLLC

(57) ABSTRACT

Compositions and methods for the therapy and diagnosis of cancer, such as breast cancer, are disclosed. Compositions may comprise one or more breast tumor proteins, immunogenic portions thereof, or polynucleotides that encode such portions. Alternatively, a therapeutic composition may comprise an antigen presenting cell that expresses a breast tumor protein, or a T cell that is specific for cells expressing such a protein. Such compositions may be used, for example, for the prevention and treatment of diseases such as breast cancer. Diagnostic methods based on detecting a breast tumor protein, or mRNA encoding such a protein, in a sample are also provided.

7 Claims, 1 Drawing Sheet

OTHER PUBLICATIONS

Figure 1A:
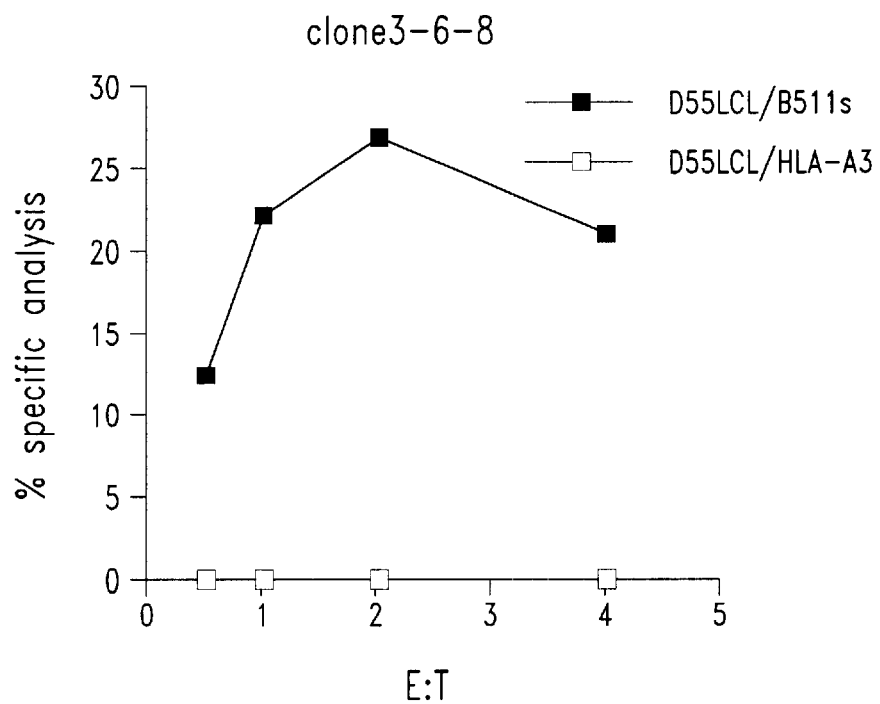

Genbank Sequence Database, Accession No. AA703778, Dec. 24, 1997.
Genbank Sequence Database, Accession No. AA722353, Jan. 2, 1998.
Genbank Sequence Database, Accession No. AA746345, Jan. 27, 1998.
Genbank Sequence Database, Accession No. AA775552, Feb. 5, 1998.
Genbank Sequence Database, Accession No. AA848022, Mar. 31, 1998.
Genbank Sequence Database, Accession No. AA856775, Jun. 9, 1998.
Genbank Sequence Database, Accession No. AA857943, Apr. 29, 1998.
Genbank Sequence Database, Accession No. AA962009, May 15, 1998.
Genbank Sequence Database, Accession No. AA971201, May 20, 1998.
Genbank Sequence Database, Accession No. AJ005890, May 15, 1998.
Genbank Sequence Database, Accession No. D50995, Sep. 14, 1995.
Genbank Sequence Database, Accession No. D59275, Aug. 28, 1995.
Genbank Sequence Database, Accession No. D80022, Feb. 9, 1996.
Genbank Sequence Database, Accession No. H21976, Jul. 6, 1995.
Genbank Sequence Database, Accession No. H21977, Jul. 6, 1995.
Genbank Sequence Database, Accession No. H25577, Jul. 10, 1995.
Genbank Sequence Database, Accession No. H25624, Jul. 10, 1995.
Genbank Sequence Database, Accession No. N48289, Feb. 14, 1996.
Genbank Sequence Database, Accession No. N49017, Feb. 14, 1996.
Genbank Sequence Database, Accession No. N54784, Jan. 28, 1997.
Genbank Sequence Database, Accession No. N59253, Feb. 23, 1996.
Genbank Sequence Database, Accession No. N62351, Mar. 1, 1996.
Genbank Sequence Database, Accession No. N76721, Apr. 2, 1996.
Genbank Sequence Database, Accession No. R75793, Jun. 6, 1995.
Genbank Sequence Database, Accession No. R78938, Jun. 9, 1995.
Genbank Sequence Database, Accession No. T21968, Aug. 5, 1996.
Genbank Sequence Database, Accession No. W02878, Apr. 18, 1996.
Genbank Sequence Database, Accession No. W72837, Oct. 16, 1996.
Genbank Sequence Database, Accession No. W72838, Oct. 16, 1996.
Genbank Sequence Database, Accession No. Z98046, Jul. 13, 1998.
Liang et al., "Differential Display and Cloning of Messenger RNAS from Human Breast Cancer *Versus* Mammary Epithelial Cell," *Cancer Research* 52:6966–6968, 1992.
Porter Jordan and Lippman, "Overview of the Biological Markers of Breast Cancer," *Breast Cancer* 8:73–100, 1994.
Schlom et al., "Strategies for the Development of Recominant Vaccines for the Immunotherapy of Breast Cancer," *Breast Cancer Research and Treatment* 38(1):27–39, 1996.
Watson and Fleming, "Isolation of Differentially Expressed Sequence Tags from Human Breast Cancer," *Cancer Research* 54(17):4598–4602, 1994.
Yee et al., "Isolation of Tyrosinase–Specific $CD8^+$ and $CD4^+$ T Cell Clones from the Peripheral Blood of Melanoma Patients Following In Vitro Stimulation with Recombinant Vaccinia Virus," *J. of Immunology* 157:4079–4086, 1996.
Hara et al., "Characterization of cell phenotype by a novel cDNA library subtraction system: Expression of $CD8\alpha$ in a mast cell–derived interleukin–4–dependent cell line," *Blood* 84(1):189–199, Jul. 1, 1994.
Porter–Jordan et al., "Overview of the biologic markers of breast cancer," *Breast Cancer* 8:73–100, 1994.
Yee et al., "Isolation of tyrosinase–specific $CD8^+$ and $CD4^+$ T cell clones from the peripheral blood of melanoma patients following in vitro stimulation with recombinant vaccinia virus," *The Journal of Immunology* 157:4079–4086, 1996.
GenBank Accession No. AA749298, "*Homo sapiens* cDNA clone Image:1271152 3', mRNA sequence," Jan. 20, 1998.

COMPOSITIONS AND METHODS FOR THE THERAPY AND DIAGNOSIS OF BREAST CANCER

REFERENCE TO RELATED APPLICATIONS

This application is a continuation-in-part of U.S. patent application Ser. No. 09/346,327, filed Jul. 2, 1999, which is a continuation-in-part of U.S. patent application Ser. No. 09/288,950, filed Apr. 9, 1999, now abandoned, which is a continuation-in-part of U.S. patent application Ser. No. 09/248,178, filed Feb. 9, 1999, which is a continuation-in-part of U.S. patent application Ser. No. 09/118,627, filed Jul. 17, 1998, which is a continuation-in-part of U.S. patent application Ser. No. 08/998,253, filed Dec. 24, 1997, now abandoned.

TECHNICAL FIELD OF THE INVENTION

The present invention relates generally to therapy and diagnosis of cancer, such as breast cancer. The invention is more specifically related to polypeptides comprising at least a portion of a breast tumor protein, and to polynucleotides encoding such polypeptides. Such polypeptides and polynucleotides may be used in compositions for prevention and treatment of breast cancer, and for the diagnosis and monitoring of such cancers.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

Briefly stated, the present invention provides compositions and methods for the diagnosis and therapy of cancer, such as breast cancer. In one aspect, the present invention provides polypeptides comprising at least a portion of a breast tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in SEQ ID NO: 1–97, 100 and 102–107; (b) variants of a sequence recited in SEQ ID NO: 1–97, 100 and 102–107; and (c) complements of a sequence of (a) or (b). In specific embodiments, the polypeptides of the present invention comprise at least a portion of a tumor protein that includes an amino acid sequence selected from the group consisting of sequences recited in SEQ ID NO: 98, 99 and 101, and variants thereof.

The present invention further provides polynucleotides that encode a polypeptide as described above, or a portion thereof (such as a portion encoding at least 15 amino acid residues of a breast tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, immunogenic compositions, or vaccines for prophylactic or therapeutic use are provided. Such compositions comprise a polypeptide or polynucleotide as described above and an immunostimulant.

The present invention further provides pharmaceutical compositions that comprise: (a) an antibody or antigen-binding fragment thereof that specifically binds to a breast tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, immunogenic compositions, or vaccines, are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Compositions are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a breast tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a breast tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4$^+$ and/or CD8$^+$ T cells isolated from a patient with one or more of: (i) a polypeptide comprising at least an immunogenic portion of a breast tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be breast cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a breast tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a breast tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

Figure 1B:
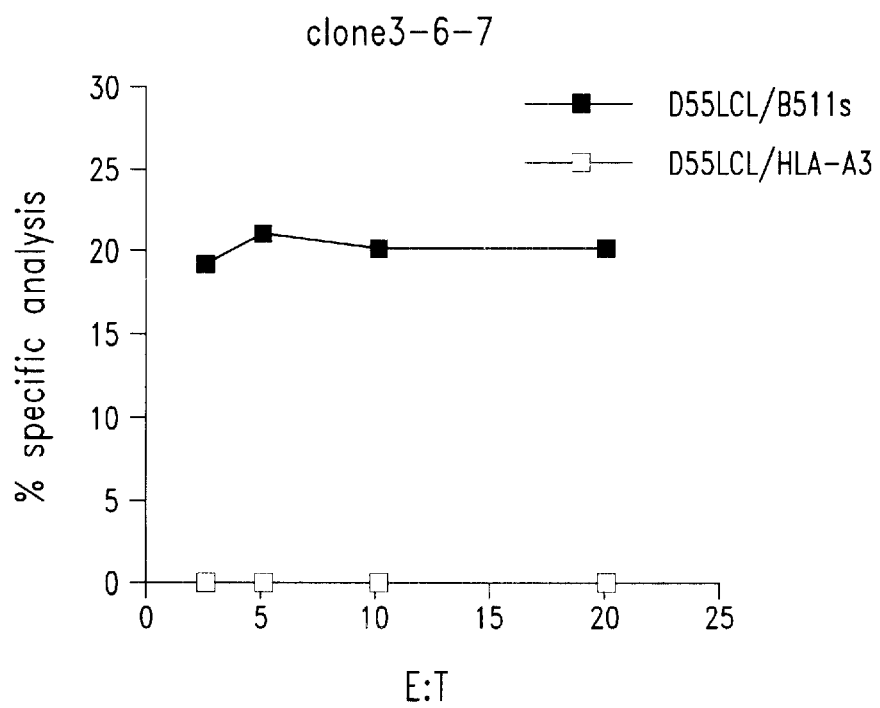

FIGS. 1A and 1B show the specific lytic activity of a first and a second B511S-specific CTL clone, respectively, measured on autologous LCL transduced with B511s (filled squares) or HLA-A3 (open squares).

SEQ ID NO: 1 is the determined 3'cDNA sequence of 1T-5120
SEQ ID NO: 2 is the determined 3'cDNA sequence of 1T-5122
SEQ ID NO: 3 is the determined 3'cDNA sequence of 1T-5123
SEQ ID NO: 4 is the determined 3'cDNA sequence of 1T-5125
SEQ ID NO: 5 is the determined 3'cDNA sequence of 1T-5126
SEQ ID NO: 6 is the determined 3'cDNA sequence of 1T-5127
SEQ ID NO: 7 is the determined 3'cDNA sequence of 1T-5129
SEQ ID NO: 8 is the determined 3'cDNA sequence of 1T-5130
SEQ ID NO: 9 is the determined 3'cDNA sequence of 1T-5133
SEQ ID NO: 10 is the determined 3'cDNA sequence of 1T-5136
SEQ ID NO: 11 is the determined 3'cDNA sequence of 1T-5137
SEQ ID NO: 12 is the determined 3'cDNA sequence of 1T-5139
SEQ ID NO: 13 is the determined 3'cDNA sequence of 1T-5142
SEQ ID NO: 14 is the determined 3'cDNA sequence of 1T-5143
SEQ ID NO: 15 is the determined 5'cDNA sequence of 1T-5120

SEQ ID NO: 16 is the determined 5'cDNA sequence of 1T-5122
SEQ ID NO: 17 is the determined 5'cDNA sequence of 1T-5123
SEQ ID NO: 18 is the determined 5'cDNA sequence of 1T-5125
SEQ ID NO: 19 is the determined 5'cDNA sequence of 1T-5126
SEQ ID NO: 20 is the determined 5'cDNA sequence of 1T-5127
SEQ ID NO: 21 is the determined 5'cDNA sequence of 1T-5129
SEQ ID NO: 22 is the determined 5'cDNA sequence of 1T-5130
SEQ ID NO: 23 is the determined 5'cDNA sequence of 1T-5133
SEQ ID NO: 24 is the determined 5'cDNA sequence of 1T-5136
SEQ ID NO: 25 is the determined 5'cDNA sequence of 1T-5137
SEQ ID NO: 26 is the determined 5'cDNA sequence of 1T-5139
SEQ ID NO: 27 is the determined 5'cDNA sequence of 1T-5142
SEQ ID NO: 28 is the determined 5'cDNA sequence of 1T-5143
SEQ ID NO: 29 is the determined 5'cDNA sequence of 1D-4315
SEQ ID NO: 30 is the determined 5'cDNA sequence of 1D-4311
SEQ ID NO: 31 is the determined 5'cDNA sequence of 1E-4440
SEQ ID NO: 32 is the determined 5'cDNA sequence of 1E-4443
SEQ ID NO: 33 is the determined 5'cDNA sequence of 1D-4321
SEQ ID NO: 34 is the determined 5'cDNA sequence of 1D-4310
SEQ ID NO: 35 is the determined 5'cDNA sequence of 1D-4320
SEQ ID NO: 36 is the determined 5'cDNA sequence of 1E-4448
SEQ ID NO: 37 is the determined 5'cDNA sequence of 1S-5105
SEQ ID NO: 38 is the determined 5'cDNA sequence of 1S-5110
SEQ ID NO: 39 is the determined 5'cDNA sequence of 1S-5111
SEQ ID NO: 40 is the determined 5'cDNA sequence of 1S-5116
SEQ ID NO: 41 is the determined 5'cDNA sequence of 1S-5114
SEQ ID NO: 42 is the determined 5'cDNA sequence of 1S-5115
SEQ ID NO: 43 is the determined 5'cDNA sequence of 1S-5118
SEQ ID NO: 44 is the determined 5'cDNA sequence of 1T-5134
SEQ ID NO: 45 is the determined 5'cDNA sequence of 1E-4441
SEQ ID NO: 46 is the determined 5'cDNA sequence of 1E-4444
SEQ ID NO: 47 is the determined 5'cDNA sequence of 1E-4322
SEQ ID NO: 48 is the determined 5'cDNA sequence of 1S-5103
SEQ ID NO: 49 is the determined 5'cDNA sequence of 1S-5107
SEQ ID NO: 50 is the determined 5'cDNA sequence of 1S-5113
SEQ ID NO: 51 is the determined 5'cDNA sequence of 1S-5117
SEQ ID NO: 52 is the determined 5'cDNA sequence of 1S-5112
SEQ ID NO: 53 is the determined cDNA sequence of 1013E11
SEQ ID NO: 54 is the determined cDNA sequence of 1013H10
SEQ ID NO: 55 is the determined cDNA sequence of 1017C2
SEQ ID NO: 56 is the determined cDNA sequence of 1016F8
SEQ ID NO: 57 is the determined cDNA sequence of 1015F5
SEQ ID NO: 58 is the determined cDNA sequence of 1017A11
SEQ ID NO: 59 is the determined cDNA sequence of 1013A11 (also known as B537S)
SEQ ID NO: 60 is the determined cDNA sequence of 1016D8
SEQ ID NO: 61 is the determined cDNA sequence of 1016D12 (also known as B532S)
SEQ ID NO: 62 is the determined cDNA sequence of 1015E8
SEQ ID NO: 63 is the determined cDNA sequence of 1015D11 (also known as B512S)
SEQ ID NO: 64 is the determined cDNA sequence of 1012H8 (also known as B533S)
SEQ ID NO: 65 is the determined cDNA sequence of 1013C8
SEQ ID NO: 66 is the determined cDNA sequence of 1014B3
SEQ ID NO: 67 is the determined cDNA sequence of 1015B2 (also known as B536S)
SEQ ID NO: 68–71 are the determined cDNA sequences of previously identified antigens
SEQ ID NO: 72 is the determined cDNA sequence of JJ9434
SEQ ID NO: 73 is the determined cDNA sequence of B535S
SEQ ID NO: 74–88 are the determined cDNA sequence of previously identified antigens
SEQ ID NO: 89 is the determined cDNA sequence of B534S
SEQ ID NO: 90 is the determined cDNA sequence of B538S
SEQ ID NO: 91 is the determined cDNA sequence of B542S
SEQ ID NO: 92 is the determined cDNA sequence of B543S
SEQ ID NO: 93 is the determined cDNA sequence of P501S
SEQ ID NO: 94 is the determined cDNA sequence of B541S
SEQ ID NO: 95 is the full-length cDNA sequence for 1016F8 (also referred to as B511S)
SEQ ID NO: 96 is the full-length cDNA sequence for 1016D12 (also referred to as B532S)
SEQ ID NO: 97 is an extended cDNA sequence for 1012H8 (also referred to as B533S)
SEQ ID NO: 98 is the amino acid sequence for B511S
SEQ ID NO: 99 is the amino acid sequence for B532S
SEQ ID NO: 100 is the determined full-length cDNA sequence for P501S
SEQ ID NO: 101 is the amino acid sequence for P501S
SEQ ID NO: 102 is the determined cDNA sequence of clone #19605, also referred to as 1017C2, showing no significant homology to any known gene
SEQ ID NO: 103 is the determined 3' end cDNA sequence for clone #19599, showing homology to the Tumor Expression Enhanced gene
SEQ ID NO: 104 is the determined 5' end cDNA sequence for clone #19599, showing homology to the Tumor Expression Enhanced gene SEQ ID NO: 105 is the determined cDNA sequence for clone #19607, showing homology to Stromelysin-3

SEQ ID NO: 106 is the determined cDNA sequence for clone #19601, showing homology to Collagen SEQ ID NO: 107 is the determined cDNA sequence of clone #19606, also referred to as B546S, showing no significant homology to any known gene

DETAILED DESCRIPTION OF THE INVENTION

As noted above, the present invention is generally directed to compositions and methods for using the compositions, for example in the therapy and diagnosis of cancer, such as breast cancer. Certain illustrative compositions described herein include breast tumor polypeptides, polynucleotides encoding such polypeptides, binding agents such as antibodies, antigen presenting cells (APCs) and/or immune system cells (e.g., T cells). A "breast tumor protein," as the term is used herein, refers generally to a protein that is expressed in breast tumor cells at a level that is at least two fold, and preferably at least five fold, greater than the level of expression in a normal tissue, as determined using a representative assay provided herein. Certain breast tumor proteins are tumor proteins that react detectably (within an immunoassay, such as an ELISA or Western blot) with antisera of a patient afflicted with breast cancer.

Therefore, in accordance with the above, and as described further below, the present invention provides illustrative polynucleotide compositions having sequences set forth in SEQ ID NO: 1–97, 100 and 102–107, illustrative polypeptide compositions having amino acid sequences set forth in SEQ ID NO: 98, 99 and 101, antibody compositions capable of binding such polypeptides, and numerous additional embodiments employing such compositions, for example in the detection, diagnosis and/or therapy of human breast cancer.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a breast tumor protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Probes and Primers

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementary stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO: 1–97, 100 and 102–107, or to any continuous portion of the sequence, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as breast tumor cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a breast tumor cDNA library) using well known techniques. Within such techniques, a library (CDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or Trichoplusia larvae in which the polypeptide of interest may be expressed (Engelhard, E. K. et al. (1994) *Proc. Natl. Acad. Sci.* 91: 3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Site-specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the antigenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U. S. Pat. No. 4,237,224, specifically incorporated herein by reference in its entirety.

Polynucleotide Amplification Techniques

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNase H while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

Biological Functional Equivalents

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0 ±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al, 1989).

3. Adeno-association Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

5. Non-viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

Antisense Oligonucleotides

The end result of the flow of genetic information is the synthesis of protein. DNA is transcribed by polymerases into messenger RNA and translated on the ribosome to yield a folded, functional protein. Thus there are several steps along the route where protein synthesis can be inhibited. The native DNA segment coding for a polypeptide described herein, as all such mammalian DNA strands, has two strands: a sense strand and an antisense strand held together by hydrogen bonding. The messenger RNA coding for polypeptide has the same nucleotide sequence as the sense DNA strand except that the DNA thymidine is replaced by uridine. Thus, synthetic antisense nucleotide sequences will bind to a mRNA and inhibit expression of the protein encoded by that mRNA.

The targeting of antisense oligonucleotides to mRNA is thus one mechanism to shut down protein synthesis, and, consequently, represents a powerful and targeted therapeutic approach. For example, the synthesis of polygalactauronase and the muscarine type 2 acetylcholine receptor are inhibited by antisense oligonucleotides directed to their respective mRNA sequences (U.S. Pat. Nos. 5,739,119 and 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., 1988; Vasanthakumar and Ahmed, 1989; Peris et al., 1998; U.S. Pat. Nos. 5,801,154; 5,789,573; 5,718,709 and 5,610,288, each specifically incorporated herein by reference in its entirety). Antisense constructs have also been described that inhibit and can be used to treat a variety of abnormal cellular proliferations, e.g. cancer (U.S. Pat. Nos. 5,747,470; 5,591,317 and 5,783,683, each specifically incorporated herein by reference in its entirety).

Therefore, in exemplary embodiments, the invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987;

Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity.

Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-ally, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes are well known in the art, and include detection of the presence of mRNA associated with an IL-5 related condition. Such RNA is detected by determining the presence of a cleavage product after treatment with a ribozyme using standard methodology.

Peptide Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass.). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11–13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

In the present invention, a polypeptide composition is also understood to comprise one or more polypeptides that are immunologically reactive with antibodies generated against a polypeptide of the invention, particularly a polypeptide having the amino acid sequence disclosed in SEQ ID NO: 98, 99 and 101, or to active fragments, or to variants or biological functional equivalents thereof.

Likewise, a polypeptide composition of the present invention is understood to comprise one or more polypeptides that are capable of eliciting antibodies that are immunologically reactive with one or more polypeptides encoded by one or more contiguous nucleic acid sequences contained in SEQ ID NO: 1–97, 100 and 102–107, or to active fragments, or to variants thereof, or to one or more nucleic acid sequences which hybridize to one or more of these sequences under conditions of moderate to high stringency. Particularly illustrative polypeptides include the amino acid sequence disclosed in SEQ ID NO: 98, 99 and 101.

As used herein, an active fragment of a polypeptide includes a whole or a portion of a polypeptide which is modified by conventional techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a breast tumor protein or a variant thereof, as described herein. As noted above, a "breast tumor protein" is a protein that is expressed by breast tumor cells. Proteins that are breast tumor proteins also react detectably within an immunoassay (such as an ELISA) with antisera from a patient with breast cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a breast tumor protein or a variant thereof Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native breast tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native breast tumor protein. A polypeptide "variant," as used herein, is a polypeptide that differs from a native breast tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% or more identity (determinined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. *New Engl. J Med.*, 336:86–91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a breast tumor protein. As used herein, an antibody, or antigen-binding fragment thereof, is said to "specifically bind" to a breast tumor protein if it reacts at a detectable level (within, for example, an ELISA) with a breast tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as breast cancer, using the representative assays provided herein. In other words, antibodies or other binding agents that bind to a breast tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a breast tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a breast tumor polypeptide, polynucleotide encoding a breast tumor polypeptide and/or an antigen presenting cell (APC) that expresses such a polypeptide. Such stimulation is performed under conditions and for a time sufficient to permit the generation of T cells that are specific for the polypeptide. Preferably, a breast tumor polypeptide or polynucleotide is present within a delivery vehicle, such as a microsphere, to facilitate the generation of specific T cells.

T cells are considered to be specific for a breast tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a breast tumor polypeptide (100 ng/ml–100 µg/ml, preferably 200 ng/ml–25 µg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a breast tumor polypeptide, polynucleotide or polypeptide-expressing APC may be $CD4^+$ and/or $CD8^+$. Breast tumor protein-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a breast tumor polypeptide, polynucleotide or APC can be expanded in number either in vitro or in vivo. Proliferation of such T cells in vitro may be accomplished in a variety of ways. For example, the T cells can be re-exposed to a breast tumor polypeptide, or a short peptide corresponding to an immunogenic portion of such a polypeptide, with or without the addition of T cell growth factors, such as interleukin-2, and/or stimulator cells that synthesize a breast tumor polypeptide. Alternatively, one or more T cells that proliferate in the presence of a breast tumor protein can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable solutions for administration to a cell or an animal, either alone, or in combination with one or more other modalities of therapy.

It will also be understood that, if desired, the nucleic acid segment, RNA, DNA or PNA compositions that express a polypeptide as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 μm) should be designed using polymers able to be degraded in vivo. Biodegradable polyalkylcyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety).

Immunogenic Compositions

In certain preferred embodiments of the present invention, immunogenic compositions, or vaccines, are provided. The immunogenic compositions will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and immunogenic compositions within the scope of the present invention may also contain other compounds, which may be biologically active or inactive. For example, one or more immunogenic portions of other tumor antigens may be present, either incorporated into a fusion polypeptide or as a separate compound, within the composition.

Illustrative immunogenic compositions may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells. It will be apparent that an immunogenic composition may comprise both a polynucleotide and a polypeptide component. Such immunogenic compositions may provide for an enhanced immune response.

It will be apparent that an immunogenic composition may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the immunogenic compositions of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the immunogenic compositions provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of an immunogenic composition as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, California, United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any immunogenic composition provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and immunogenic compositions to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a breast tumor protein (or portion or other variant thereof) such that the breast tumor polypeptide, or an immunogenic portion thereof, is expressed on the cell surface. Such transfection may take place ex vivo, and a composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the breast tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Immunogenic compositions and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a immunogenic composition or pharmaceutical composition may be stored in a freeze-dried condition requiring only the addition of a sterile liquid carrier immediately prior to use.

Cancer Therapy

In further aspects of the present invention, the compositions described herein may be used for immunotherapy of cancer, such as breast cancer. Within such methods, pharmaceutical compositions and immunogenic compositions are typically administered to a patient. As used herein, a "patient" refers to any warm-blooded animal, preferably a human. A patient may or may not be afflicted with cancer. Accordingly, the above pharmaceutical compositions and immunogenic compositions may be used to prevent the development of a cancer or to treat a patient afflicted with a cancer. A cancer may be diagnosed using criteria generally accepted in the art, including the presence of a malignant tumor. Pharmaceutical compositions and immunogenic compositions may be administered either prior to or following surgical removal of primary tumors and/or treatment such as administration of radiotherapy or conventional chemotherapeutic drugs. Administration may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and immunogenic compositions may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such immunogenic compositions should also be capable of causing an immune response that leads to an improved clinical outcome (e.g., more frequent remissions, complete or partial or longer disease-free survival) in treated patients as compared to non-treated patients. In general, for pharmaceutical compositions and immunogenic compositions comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a breast tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnosis

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use breast tumor polypeptides to detect antibodies that bind to such polypeptides in a biological sample. The detection of such breast tumor protein specific antibodies may correlate with the presence of a cancer.

A cancer may also, or alternatively, be detected based on the presence of T cells that specifically react with a breast tumor protein in a biological sample. Within certain methods, a biological sample comprising $CD4^+$ and/or $CD8^+$ T cells isolated from a patient is incubated with a breast tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 μg/ml). It may be desirable to incubate another aliquot of a T cell sample in the absence of breast tumor polypeptide to serve as a control. For CD4$^+$ T cells, activation is preferably detected by evaluating proliferation of the T cells. For CD8$^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a breast tumor protein in a biological sample. For example, at least two oligonucleotide primers may be employed in a polymerase chain reaction (PCR) based assay to amplify a portion of a breast tumor cDNA derived from a biological sample, wherein at least one of the oligonucleotide primers is specific for (i.e., hybridizes to) a polynucleotide encoding the breast tumor protein. The amplified cDNA is then separated and detected using techniques well known in the art, such as gel electrophoresis. Similarly, oligonucleotide probes that specifically hybridize to a polynucleotide encoding a breast tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a breast tumor protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–97, 100 and 102–107. Techniques for both PCR based assays and hybridization assays are well known in the art (see, for example, Mullis et al., *Cold Spring Harbor Symp. Quant. Biol.,* 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple breast tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a breast tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a breast tumor protein in a biological sample. Such kits generally comprise at least one oligonucleotide probe or primer, as described above, that hybridizes to a polynucleotide encoding a breast tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a breast tumor protein.

The following Examples are offered by way of illustration and not by way of limitation.

EXAMPLE 1

Isolation and Characterization of Breast Tumor Polypeptides

This Example describes the isolation of breast tumor polypeptides from a breast tumor cDNA library.

A human breast tumor cDNA expression library was constructed from a pool of breast tumor poly A$^+$ RNA from three patients using a Superscript Plasmid System for CDNA Synthesis and Plasmid Cloning kit (BRL Life Technologies, Gaithersburg, Md. 20897) following the manufacturer's protocol. Specifically, breast tumor tissues were homogenized with polytron (Kinematica, Switzerland) and total RNA was extracted using Trizol reagent (BRL Life Technologies) as directed by the manufacturer. The poly A$^+$ RNA was then purified using a Qiagen oligotex spin column MRNA purification kit (Qiagen, Santa Clarita, Calif. 91355)

according to the manufacturer's protocol. First-strand cDNA was synthesized using the NotI/Oligo-dT18 primer. Double-stranded cDNA was synthesized, ligated with EcoRI/BstX I adaptors (Invitrogen, Carlsbad, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen, Carlsbad, Calif.) and transformed into ElectroMax *E. coli* DH10B cells (BRL Life Technologies) by electroporation.

Using the same procedure, a normal human breast cDNA expression library was prepared from a pool of four normal breast tissue specimens. The cDNA libraries were characterized by determining the number of independent colonies, the percentage of clones that carried insert, the average insert size and by sequence analysis. The breast tumor library contained $1.14 \times 10^7$ independent colonies, with more than 90% of clones having a visible insert and the average insert size being 936 base pairs. The normal breast cDNA library contained $6 \times 10^6$ independent colonies, with 83% of clones having inserts and the average insert size being 1015 base pairs. Sequencing analysis showed both libraries to contain good complex cDNA clones that were synthesized from mRNA, with minimal rRNA and mitochondrial DNA contamination sequencing.

cDNA library subtraction was performed using the above breast tumor and normal breast cDNA libraries, as described by Hara et al. (*Blood*, 84:189–199, 1994) with some modifications. Specifically, a breast tumor-specific subtracted cDNA library was generated as follows. Normal breast cDNA library (70 μg) was digested with EcoRI, NotI, and SfuI, followed by a filling-in reaction with DNA polymerase Klenow fragment. After phenol-chloroform extraction and ethanol precipitation, the DNA was dissolved in 100 μl of $H_2O$, heat-denatured and mixed with 100 μl (100 μg) of Photoprobe biotin (Vector Laboratories, Burlingame, Calif.), the resulting mixture was irradiated with a 270 W sunlamp on ice for 20 minutes. Additional Photoprobe biotin (50 μl) was added and the biotinylation reaction was repeated. After extraction with butanol five times, the DNA was ethanol-precipitated and dissolved in 23 μl $H_2O$ to form the driver DNA.

To form the tracer DNA, 10 μg breast tumor cDNA library was digested with BamHI and XhoI, phenol chloroform extracted and passed through Chroma spin-400 columns (Clontech). Following ethanol precipitation, the tracer DNA was dissolved in 5 μl $H_2O$. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl $H_2O$, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK⁺ (Stratagene, La Jolla, Calif. 92037) and transformed into ElectroMax *E. coli* DH10B cells by electroporation to generate a breast tumor specific subtracted cDNA library.

To analyze the subtracted cDNA library, plasmid DNA was prepared from 100 independent clones, randomly picked from the subtracted breast tumor specific library and characterized by DNA sequencing with a Perkin Elmer/Applied Biosystems Division Automated Sequencer Model 373A (Foster City, Calif.). Thirty-eight distinct cDNA clones were found in the subtracted breast tumor-specific cDNA library. The determined 3' cDNA sequences for 14 of these clones are provided in SEQ ID NO: 1–14, with the corresponding 5' cDNA sequences being provided in SEQ ID NO: 15–28, respectively. The determined one strand (5' or 3') cDNA sequences for the remaining clones are provided in SEQ ID NO: 29–52. Comparison of these cDNA sequences with known sequences in the gene bank using the EMBL and GenBank databases (Release 97) revealed no significant homologies to the sequences provided in SEQ ID NO: 3, 10, 17, 24 and 45–52. The sequences provided in SEQ ID NO: 1, 2, 4–9, 11–16, 18–23, 25–41, 43 and 44 were found to show at least some degree of homology to known human genes. The sequence of SEQ ID NO: 42 was found to show some homology to a known yeast gene.

cDNA clones isolated in the breast subtraction described above were colony PCR amplified and their mRNA expression levels in breast tumor, normal breast and various other normal tissues were determined using microarray technology (Synteni, Fremont, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity.

Data was analyzed using GEMTOOLS Software. Twenty one distinct cDNA clones were found to be over-expressed in breast tumor and expressed at low levels in all normal tissues tested. The determined partial cDNA sequences for these clones are provided in SEQ ID NO: 53–73. Comparison of the sequences of SEQ ID NO: 53, 54 and 68–71 with those in the gene bank as described above, revealed some homology to previously identified human genes. No significant homologies were found to the sequences of SEQ ID NO: 55–67, 72 (referred to as JJ 9434) and 73 (referred to as B535S). In further studies, full length cDNA sequences were obtained for the clones 1016F8 (SEQ ID NO: 56; also referred to as B511S) and 1016D12 (SEQ ID NO: 61; also referred to as B532S), and an extended cDNA sequence was obtained for 1012H8 (SEQ ID NO: 64; also referred to as B533S). These cDNA sequences are provided in SEQ ID NO: 95–97, respectively, with the corresponding amino acid sequences for B511S and B532S being provided in SEQ ID NO: 98 and 99, respectively.

Analysis of the expression of B511S in breast tumor tissues and in a variety of normal tissues (skin, PBMC, intestine, breast, stomach, liver, kidney, fetal tissue, adrenal gland, salivary gland, spinal cord, large intestine, small intestine, bone marrow, brain, heart, colon and pancreas) by microarray, northern analysis and real time PCR, demonstrated that B511S is over-expressed in breast tumors, and normal breast, skin and salivary gland, with expression being low or undetectable in all other tissues tested.

Analysis of the expression of B532S in breast tumor tissue and in a variety of normal tissues (breast, PBMC, esophagus, HMEC, spinal cord, bone, thymus, brain, bladder, colon, liver, lung, skin, small intestine, stomach, skeletal muscle, pancreas, aorta, heart, spleen, kidney, salivary gland, bone marrow and adrenal gland) by microarray, Northern analysis and real time PCR, demonstrated that B532S is over-expressed in 20–30% of breast tumors with expression being low or undetectable in all other tissues tested.

In a further experiment, cDNA fragments were obtained from two subtraction libraries derived by conventional subtraction, as described above and analyzed by DNA microarray. In one instance the tester was derived from primary breast tumors, referred to as Breast Subtraction 2, or BS2. In the second instance, a metastatic breast tumor was employed as the tester, referred to as Breast Subtraction 3, or BS3. Drivers consisted of normal breast.

cDNA fragments from these two libraries were submitted as templates for DNA microarray analysis, as described above. DNA chips were analyzed by hybridizing with fluorescent probes derived from mRNA from both tumor and normal tissues. Analysis of the data was accomplished by creating three groups from the sets of probes, referred to as breast tumor/mets, normal non-breast tissues, and metastatic breast tumors. Two comparisons were performed using the modified Gemtools analysis. The first comparison was to identify templates with elevated expression in breast tumors. The second was to identify templates not recovered in the first comparison that yielded elevated expression in metastatic breast tumors. An arbitrary level of increased expression (mean of tumor expression versus the mean of normal tissue expression) was set at approximately 2.2.

In the first round of comparison to identify over-expression in breast tumors, two novel gene sequences were identified, hereinafter referred to as B534S and B538S (SEQ ID NO: 89 and 90, respectively), together with six sequences that showed some degree of homology to previously identified genes (SEQ ID NO: 74–79). The sequences of SEQ ID NO: 75 and 76 were subsequently determined to be portions of B535S (SEQ ID NO: 73). In a second comparison to identify elevated expression in metastatic breast tumors, five novel sequences were identified, hereinafter referred to as B535S, B542S, B543S, P501S and B541S (SEQ ID NO: 73 and 91–94, respectively), as well as nine gene sequences that showed some homology to known genes (SEQ ID NO: 80–88). Clone B534S and B538S (SEQ ID NO: 89 and 90) were shown to be over-expressed in both breast tumors and metastatic breast tumors.

In a subsequent series of studies, 457 clones from Breast Subtraction 2 were analyzed by microarray on Breast Chip 3. As described above, a first comparison to identify over-expression in breast tumors over normal non-breast tissues was performed. This analysis yielded six cDNA clones that demonstrated elevated expression in breast tumor over normal non-breast tissues. Two of these clones, referred to as 1017C2 (SEQ ID NO: 102) and B546S (SEQ ID NO: 107) do not share significant homology to any known genes. Clone B511S also showed over-expression in breast tumor, which was previously described as 1016F8, with the determined cDNA sequence provided in SEQ ID NO: 95 and the amino acid sequence provided in SEQ ID NO: 98. The remaining four clones over-expressed in breast tumor were found to share some degree of homology to Tumor Expression Enhanced Gene (SEQ ID NO: 103 and 104) Stromelysin-3 (SEQ ID NO: 105) or Collagen (SEQ ID NO: 106).

In the second comparison to determine genes with elevated expression in metastatic breast tumors over non-breast normal tissues, a profile similar to the first comparison was derived. The two putatively novel clones, 1017C2 and B546S, SEQ ID NO: 102 and 107, respectively, were overexpressed in metastatic breast tumors. In addition, Tumor Expression Enhanced Gene and B511S also showed elevated expression in metastatic breast tumors.

As described in U.S. patent application Ser. No. 08/806,099, filed Feb. 25, 1997, the antigen P501S was isolated by subtracting a prostate tumor cDNA library with a normal pancreas cDNA library and with three genes found to be abundant in a previously subtracted prostate tumor specific cDNA library: human glandular kallikrein, prostate specific antigen (PSA), and mitochondria cytochrome C oxidase subunit II. The determined full-length cDNA sequence for P501S is provided in SEQ ID NO: 100, with the corresponding amino acid sequence being provided in SEQ ID NO: 101. Expression of P501S in breast tumor was examined by microarray analysis. Over-expression was found in prostate tumor, breast tumor and metastatic breast tumor, with negligible to low expression being seen in normal tissues. This data suggests that P501S may be over-expressed in various breast tumors as well as in prostate tumors.

EXAMPLE 2

Generation of Human CD8+ Cytotoxic T-cells that Recognize Antigen Presenting Cells Expressing Breast Tumor Antigens This Example illustrates the generation of T cells that recognize target cells expressing the antigen B511S, also known as 1016-F8 (SEQ ID NO: 95). Human CD8+ T cells were primed in-vitro to the B511S gene product using dendritic cells infected with a recombinant vaccinia virus engineered to express B511S as follows (also see Yee et al., Journal of Immunology (1996) 157 (9):4079–86). Dendritic cells (DC) were generated from peripheral blood derived monocytes by differentiation for 5 days in the presence of 50 $\mu$g/ml GMCSF and 30 $\mu$g/ml IL-4. DC were harvested, plated in wells of a 24-well plate at a density of $2\times10^5$ cells/well and infected for 12 hours with B511S expressing vaccinia at a multiplicity of infection of 5. DC were then matured overnight by the addition of 3 $\mu$g/ml CD40-Ligand and UV irradiated at 100 $\mu$W for 10 minutes. CD8+ T cells were isolated using magnetic beads, and priming cultures were initiated in individual wells (typically in 24 wells of a 24-well plate) using $7\times10^5$ CD8+ T cells and $1\times10^6$ irradiated CD8-depleted PBMC. IL-7 at 10 ng/ml was added to cultures at day 1. Cultures were re-stimulated every 7–10 days using autologous primary fibroblasts retrovirally transduced with B511S and the costimulatory molecule B7.1. Cultures were supplemented at day 1 with 15 I.U. of IL-2. Following 4 such stimulation cycles, CD8+ cultures were tested for their ability to specifically recognize autologous fibroblasts transduced with B511S using an interferon-γ Elispot assay (see Lalvani et al J. Experimental Medicine (1997) 186:859–965). Briefly, T cells from individual microcultures were added to 96-well Elispot plates that contained autologous fibroblasts transduced to express either B511S or as a negative control antigen EGFP, and incubated overnight at 37° C.; wells also contained IL-12 at 10 ng/ml. Cultures were identified that specifically produced interferon-γ only in response to B511S transduced fibroblasts; such lines were further expanded and also cloned by limiting dilution on autologous B-LCL retrovirally transduced with B511S. Lines and clones were identified that could specifically recognize autologous B-LCL transduced with B511S but not autologous B-LCL transduced with the control antigens EGFP or HLA-A3. An example demonstrating the ability of human CTL cell lines derived from such experiments to specifically recognize and lyse B511S expressing targets is presented in FIG. 1.

EXAMPLE 3

Preparation and Characterization of Antibodies Against Breast Tumor Polypeptides Polyclonal antibodies against the breast tumor antigens B511S and B532S were prepared as follows.

The breast tumor antigen expressed in an *E. coli* recombinant expression system was grown overnight in LB broth with the appropriate antibiotics at 37° C. in a shaking incubator. The next morning, 10 ml of the overnight culture was added to 500 ml to 2×YT plus appropriate antibiotics in a 2L-baffled Erlenmeyer flask. When the Optical Density (at 560 nm) of the culture reached 0.4–0.6, the cells were induced with IPTG (1 mM). Four hours after induction with IPTG, the cells were harvested by centrifugation. The cells were then washed with phosphate buffered saline and centrifuged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin such as HiPrepQ (Biorad) was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of breast tumor antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12–24 hours followed by centrifugation.

Ninety-six well plates were coated with breast tumor antigen by incubating with 50 microliters (typically 1 microgram) of recombinant protein at 4° C. for 20 hours. 250 microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the colorimetric reaction was stopped with 100 microliters of 1N $H_2SO_4$ and read immediately at 450 nm. The polyclonal antibodies prepared against B511S and B532S showed immunoreactivity to B511S and B532S, respectively.

Immunohistochemical (IHC) analysis of B511S expression in breast cancer and normal breast specimens was performed as follows. Paraffin-embedded formal fixed tissue was sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody was added to each section for 25 min at indicated concentrations followed by a 25 min incubation with either an anti-rabbit or anti-mouse biotinylated antibody. Endogenous peroxidase activity was blocked by three 1.5 min incubations with hydrogen peroxide. The avidin biotin complex/horseradish peroxidase (ABC/HRP) system was used along with DAB chromagen to visualize antigen expression. Slides were counterstained with hematoxylin.

A summary of real-time PCR and immunohistochemical analysis of B511S expression in normal and breast tumor tissues is presented in Table 2 below. B511S expression was detected in normal breast and breast tumor tissues, as well as in skin. B511S protein expression was also detected in colon, but neither protein nor mRNA was detected in a panel of normal tissues that includes kidney, brain, liver, lung, heart and bone marrow.

TABLE 2

| Tissue type | IHC staining | mRNA analysis |
| --- | --- | --- |
| Breast tumor | Positive | Positive |
| Normal breast | Positive | Positive |
| Skin | Positive (apocrine only) | Negative |
| Colon | Positive | Negative |
| Kidney | Negative | Negative |
| Brain | Negative | Negative |
| Liver | Negative | Negative |
| Lung | Negative | Negative |
| Heart | Negative | Negative |
| Bone marrow | Negative | Negative |

EXAMPLE 8

Protein Expression of Breast Tumor Antigens

This example describes the expression and purification of the breast tumor antigen B511S in mammalian cells.

Full-length B511S (SEQ ID NO: 95) was subcloned into the mammalian expression vectors pCEP4 (Invitrogen). This construct was transfected into HEK293 cells (ATCC) using Fugene 6 reagent (Roche). Briefly, the HEK cells were plated at a density of 100,000 cells/ml in DMEM (Gibco) containing 10% FBS (Hyclone) and grown overnight. The following day, 2 µl of Fugene 6 was added to 100 µl of DMEM containing no FBS and incubated for 15 minutes at room temperature. The Fugene 6/DMEM mixture was added to 1 µg of B511S/pCEP4 plasmid DNA and incubated for 15 minutes at room temperature. The Fugene/DNA mix was then added to the HEK293 cells and incubated for 48–72 hours at 37° C. with 7% $CO_2$. Cells were rinsed with PBS, then collected and pelleted by centrifugation.

For Western blot analysis, whole cell lysates were generated by incubating the cells in Triton-X100 containing lysis buffer for 30 minutes on ice. Lysates were then cleared by centrifugation at 10,000 rpm for 5 minutes at 4° C. Samples were diluted with SDS_PAGE loading buffer containing beta-mercaptoethanol, and boiled for 10 minutes prior to loading the SDS_PAGE gel. Proteins were transferred to nitrocellulose and probed using Protein A purified anti-B511S rabbit polyclonal sera (prepared as described above) at a concentration of 1 μg/ml. The blot was revealed with a goat anti-rabbit Ig coupled to HRP followed by incubation in ECL substrate. Expression of B511S was detected in the the HEK293 lysates transfected with B511S, but not in control HEK293 cells transfected with vector alone.

For FACS analysis, cells were washed further with ice cold staining buffer. Next the cells were incubated for 30 minutes on ice with 10 μg/ml of Protein A purified anti-B511S polyclonal sera. The cells were washed 3 times with staining buffer and then incubated with a 1:100 dilution of a goat anti-rabbit Ig (H+L)-FITC reagent (Southern Biotechnology) for 30 minutes on ice. Following 3 washes, the cells were resuspended in staining buffer containing Propidium Iodide (PI), a vital stain that allows for identification of permeable cells, and then analyzed by FACS. Surface expression of B511S was observed.

EXAMPLE 4

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed:

1. An isolated polynucleotide comprising SEQ ID NO:97.

2. An isolated polynucleotide complementary to a polynucleotide according to claim 1.

3. An expression vector, comprising the polynucleotide according to claim 1.

4. A host cell transformed or transfected with an expression vector according to claim 3.

5. A composition comprising an polynucleotide according to claim 1 or 2 in combination with a physiologically acceptable carrier.

6. An oligonucleotide comprising 10 to 40 contiguous nucleotides of SEQ ID NO: 97 or the complement thereof.

7. A diagnostic kit, comprising:

(a) an oligonucleotide according to claim 6; and (b) a diagnostic reagent for use in a polymerase chain reaction or hybridization assay.

* * * * *

UNITED STATES PATENT AND TRADEMARK OFFICE
CERTIFICATE OF CORRECTION

PATENT NO. : 6,432,707 B1
DATED : August 13, 2002
INVENTOR(S) : Steven G. Reed et al.

It is certified that error appears in the above-identified patent and that said Letters Patent is hereby corrected as shown below:

Title page,
Item [56], References Cited, OTHER PUBLICATIONS, Schlom et al., "Strategies for the Development of Recominant Vaccines for the Immunotherapy of Breast Cancer," *Breast Cancer Research and Treatment* 38(1):27-39, 1996." should read -- Schlom et al., Strategies for the Development of Recombinant Vaccines for the Immunotherapy of Breast Cancer," *Breast Cancer Research and Treatment* 38(1):27-39, 1996. --.

Column 151,
Line 38, "A composition comprising an polynucleotide" should read -- A composition comprising a polynucleotide --.

Signed and Sealed this

Eighteenth Day of February, 2003

JAMES E. ROGAN
*Director of the United States Patent and Trademark Office*

SEQUENCE LISTING

<160> NUMBER OF SEQ ID NOS: 107

<210> SEQ ID NO 1
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 1

```
tttttttttt tttttaggag aactgaatca aacagatttt attcaacttt ttagatgagg      60
aaaacaaatn atacgaaatn ngtcataaga aatgctttct tataccacta tctcaaacca     120
ctttcaatat tttacaaaat gctcacgcag caaatatgaa aagctncaac acttcccttt     180
gttaacttgc tgcaatnaat gcaactttaa canacataca aatttcttct gtatcttaaa     240
agttnaatta ctaattttaa tgatnttnct caagatnttt attcatatac ttttaatgac     300
tcnttgccna tacatacnta ttttctttac tttttttta cnatnggcca acagctttca     360
ngcagnccnc aaaaatctta ccggttaatt acacggggtt gt                       402
```

<210> SEQ ID NO 2
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 2

```
tttttttttt tttttaaag gtacacattt cttttcatt ctgtttnatg cagcaaataa       60
ttcgttggca tcttctctgt gatgggcagc ttgctaaaat tanactcagg cccttagct     120 ncatttccaa ctnagcccac gctttcaacc nngccnaaca aagaaaatca gttngggtta    180
aattctttgc tgganacaaa gaactacatt cctttgtaaa tnatgctttg tttgctctgt   240
```

```
gcaaacncag attgaaggga anaagganac ttntggggac ggaaacaact ngnagaagca      300 ggannccgccc agggncattt cctcaccatg cttaatcttg cnctcacttg cngggcacca    360
ttaaacttgg tgcaaaaggc gcaattggtg nanggaaccc cacaccttcc ttaaaaagca    420
gggc                                                                  424

<210> SEQ ID NO 3
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 3
tttttttttt ttttcccaa tttaaaaaag ccttttcat acttcaatta caccanactt      60
aatnatttca tgagtaaatc ngacattatt atttnaaaat ttgcatattt aaaatttgna    120
tcanttactt ccagactgtt tgcanaatga agggaggatc actcaagngc tgatctcnca    180
ctntctgcag tctnctgtcc tgtgcccggn ctaatggatc gacactanat ggacagntcn    240
cagatcttcc gttcttntcc cttccccaat ttcncaccnc tccccttctt nccgggatcn   300
tttggggaca tgntaatttt gcnatcctta aaccctgccc gccangggtc ccnanctcag   360
gggtggttaa tgttcgncng gcttnttgac cnctgcgcc ctttnantcc naacccccaag   420 c                                                                   421

<210> SEQ ID NO 4
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 4
tttttttatt ttttttttcta tttntnntat ttnntgnggt tcctgtgtgt aattagnang    60
tgtgtatgcg tangtacnta tgtntgcata tttaacctgt tnccttttcca tttttaaaat   120 aaaatctcaa natngtantt ggttnatggg agtaaanaga gactatngat naattttaac   180
atggacacng tgaaatgtag ccgctnatca ntttaaaact tcattttgaa ggccttttnc   240
cctccnaata aaaatnccng gccctactgg gttaagcaac attgcatntc taaagaaacc   300
acatgcanac nagttaaacc tgtgnactgg tcangcaaac cnanntggaa nanaagggnn   360
ttcnccccan ggacantcng aatttttta acaaattacn atncccccc nggggagcc     420 tgt                                                                 423

<210> SEQ ID NO 5
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 5
acgaccacct natttcgtat ctttcaactc ttttcgaccg gacctcttat tcggaagcgt     60
```

-continued

| | |
|---|---|
| tccaggaaga caggtctcaa cttagggatc agatcacgtt atcaacgctc tgggatcgct | 120 |
| gcaacctggc acttcaagga agtgcaccga tnacgtctag accggccaac acagatctag | 180 |
| aggtggccaa ctgatcactg taggagctga ctggcaanan tcaaccgggc cccaaccnag | 240 |
| agtgaccaan acnaccattn aggatcaccc acaggcactc ctcgtcctag ggccaaccna | 300 |
| ccaaacggct ggccaatggg ggggtttaat atttggttna aaaattgatt ttaaa | 355 |

<210> SEQ ID NO 6
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 6

| | |
|---|---|
| tttttttttt ttttttggaca ggaagtaaaa tttattggtn antattaana gggggggcagc | 60 |
| acattggaag ccctcatgan tgcagggccc gccacttgtc cagagggcca cnattgggga | 120 |
| tgtacttaac cccacagccn tctgggatna gccgcttttc agccaccatn tcttcaaatt | 180 |
| catcagcatt aaacttggta aancccccact tctttaagat ntgnatcttc tggcggccag | 240 |
| naaacttgaa cttggccctg cgcagggcct caatcacatg ctccttgttc tgcagcttgg | 300 |
| tgcgnaagga cntaatnact tggccnatgt gaaccctggc cacantgccc tggggctttc | 360 |
| caaaggcacc tcgcaagcct ntttggancc tgnccgcccc ngcacaggga caacatcttg | 420 |
| ttt | 423 |

<210> SEQ ID NO 7
<211> LENGTH: 410
<212> TYPE: DNA
<213> ORGANISM: Homo sapien
<220> FEATURE:
<221> NAME/KEY: misc_feature
<222> LOCATION: (1)...(410)
<223> OTHER INFORMATION: n = A,T,C or G

<400> SEQUENCE: 7

| | |
|---|---|
| ttcgcactgg ctaaaacaaa ccgccttgca aagttngaaa aatttatcaa tggaccaaat | 60 |
| aatgctcata tccnacaagt tggtgaccgt tnttatnata aaaaaatgta tnatgctcct | 120 |
| nanttgttgt acaataatgt tccaatttng gacnttcggc atctaccctg gttcacctgg | 180 |
| gtaaatatca ggcagctttt gatggggcta ggaaagctaa cagtactcga acatgggaaa | 240 |
| gaggtctgct tcgccngtgt anatgggaaa naattccgtc ttgctcngat ttgtggactt | 300 |
| catattgttg tacatgcaga tgaatnngaa gaacttgtca actactatca ggatcgtggc | 360 |
| ttttttnnaaa agctnatcac catgttggaa gcggcactng gacttgagcg | 410 |

<210> SEQ ID NO 8
<211> LENGTH: 274
<212> TYPE: DNA
<213> ORGANISM: Homo sapien
<220> FEATURE:
<221> NAME/KEY: misc_feature
<222> LOCATION: (1)...(274)
<223> OTHER INFORMATION: n = A,T,C or G

<400> SEQUENCE: 8

| | |
|---|---|
| tttttttttt ttttttaggtc atacatattt tttattataa canatatntg tatatacata | 60 |
| taatatatgt gtatatatcc acgtgtgtgt gtgtgtatca aaaacaacan aantttagtg | 120 |

```
atctatatct ntngctcaca tatgcatggg agataccagt aaaaaataag tnaatctcca        180
taatatgttt taaaactcan anaaatcnga gagactnaaa gaaaacgttn atcannatga        240
ttgtngataa tcttgaanaa tnacnaaaac atat                                   274

<210> SEQ ID NO 9
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 9 ttttttttttt ttttgtgcct tattgcaccg gcnanaactt ctagcactat attaaactca       60
ataagagtga taagtgtgaa atccttgcc ttctctttaa tcttaatgna naggcatctg        120
gtttttcacc attaantgta ataatggctn tatgtatttt tatnnatggt cttnatggag      180
ttaaaaaagt tttcctctnt ccctngttat ctaaagtttt tnatcaaaaa tgggtataat      240
atttngttca gtacttttnc ctgcacctat agatatgatn ctgttatttt tcttcttng       300 cctnnanata tgatggatna ca                                              322

<210> SEQ ID NO 10
<211> LENGTH: 425
<212> TYPE: DNA
<213> ORGANISM: Homo sapien
<220> FEATURE:
<221> NAME/KEY: misc_feature
<222> LOCATION: (1)...(425)
<223> OTHER INFORMATION: n = A,T,C or G

<400> SEQUENCE: 10 ttttttttttt ttttttattct gcagccatta aatgctgaac actagatnct tatttgtgga    60
ggtcacaaaa taagtacaga atatnacaca cgccctgccc ataaaaagca cagctcccag     120
ttctatattt acaatatctc tggaattcca ccttcccttc taatttgact aatatttctg     180
cttctcaggc agcagcgcct tctggcaacc ataagaacca acntgnggac taggtcggtg     240
ggccaaggat caggaaacag aanaatggaa gnagcccccn tgacnctatt aanctntnaa     300
actatctnaa ctgctagttt tcaggctttta aatcatgtaa natacgtgtc cttnttgctg    360
caaccggaag catcctagat ggtacactct ctccaggtgc caggaaaaga tcccaaatng    420 caggn                                                                425

<210> SEQ ID NO 11
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 11
ttttnttant ttttttancc nctnntccnn tntgttgnag ggggtaccaa atttcttat       60 ttaaaggaat ggtacaaatc aaaaaactta atttaatttt tngtacaac ttatagaaaa     120 ggttaaggaa accccaacat gcatgcactg ccttggtaac cagggnattc cccncggct     180 ntggggaaat tagcccaang ctnagctttc attatcactn tcccccaggg tntgcttttc   240
```

-continued

```
aaaaaaattt nccgccnagc cnaatccggg cnctcccatc tggcgcaant tggtcacttg      300
gtcccccnat tctttaangg cttncacctn ctcattcggg tnatgtgtct caattaaatc      360
ccacngatgg gggtcattt tntcnnttag ccagtttgtg nagttccgtt attganaaaa      420 ccan                                                                   424
```

<210> SEQ ID NO 12
<211> LENGTH: 426
<212> TYPE: DNA
<213> ORGANISM: Homo sapien
<220> FEATURE:
<221> NAME/KEY: misc_feature
<222> LOCATION: (1)...(426)
<223> OTHER INFORMATION: n = A,T,C or G

<400> SEQUENCE: 12

```
tttttttttt ttttncttaa aagcttttat ctcctgctta cattacccat ctgttcttgc      60
atgttgtctg cttttttccac tagagcccctt aacaacttaa tcatggttat tttaagggct   120
ctaataattc cnaaactggt atcataaata agtctcgttc tnatgcttgt tttctctcta    180
tcacactgtg ttngttgctt tttnacatgc tttgtaattt ttggctgaaa gctgaaaaat   240
nacatacctg gttntacaac ctgaggtaan cagccttnta gtgtgaggtt ttatatntta    300
ctggctaaga gctnggcnct gttnantant tgttgtanct ntatatgcca naggctttna   360
tttccnctng tgtccttgct tnagtacccc attnttttag gggttccccta naaactctat   420 ctnaat                                                                426
```

<210> SEQ ID NO 13
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 13

```
tttttttttt tttttnagat agactctcac tctttcgccc aggctggagt gcagtggcgc      60
aatcaaggct cactgcaacc tctgccttat aaagcatttn ctaaaggtac aagctaaatt    120
ttaaaaatat ctctncacaa ctaatgtata acaaaaatta gttctacctc ataaacncnt    180
ggctcagccc tcgnaacaca tttccctgtt ctcaactgat gaacactcca naaacagaac   240
anatntaagc ttttccaggc ccagaaaagc tcgcgagggg atttgctntg tgtgtgacac    300
acttgccacc ctgtggcagc acagctccac acntgctttg ggccgcattt gcaagttctc    360 tgtaanccccc ctgnaagacc cggatcagct gggtngaaat tgcangcnct cttttggca   419
```

<210> SEQ ID NO 14
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 14

```
aanccattgc caagggtatc cggaggattg tggctgtcac aggtnccgag gcccanaagg     60
ccctcaggaa agcaaagagc ttgaaaaatg tctctctgtc atggaagccn aagtgaaggc    120
tcanactgct ccaacaagga tntgcanagg gagatcgcta accttggaga ggccctggcc   180
```

```
actgcagtcn tcccccantg gcagaaggat gaattgcggg agactctcan atcccttang      240
gaaggtcgtg gatnacttgg accgagcctc nnaagccaat ntccagaaca agtgttggag      300
aagacaaagc anttcatcga cgccaacccc naccggcctc tnttctcctg ganattgana      360
gcggcgcccc cgcccagggc cttaataanc cntgaagctn                            400
```

```
<210> SEQ ID NO 15
<211> LENGTH: 395
<212> TYPE: DNA
<213> ORGANISM: Homo sapien
<220> FEATURE:
<221> NAME/KEY: misc_feature
<222> LOCATION: (1)...(395)
<223> OTHER INFORMATION: n = A,T,C or G

<400> SEQUENCE: 15
tgctttgctg cgtccaggaa gattagatng aanaatacat attgatttgc caaatgaaca       60
agcgagatta gacntactga anatccatgc aggtcccatt acaaagcatg gtgaaataga      120
tgatgaagca attgtgaagc tatcggatgg ctttnatgga gcagatctga aaatgtttg      180 tactgaagca ggtatgttcg caattcgtgc tgatcatgat tttgtagtac aggaagactt      240
catgaaagcg tcagaanag tggctnattc tnaaagctgg agtctaaatt ggacnacnac      300
ctntgtattt actgttggan ttttgatgct gcatgacaga ttttgcttan tgtaaaaatn      360
aagttcaaga aaattatgtt agttttggcc attat                                 395
```

```
<210> SEQ ID NO 16
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 16
ccaccactaa aatcctggct gagccctacn agtacctgtg cccctccccc aggacgagat       60
nagggcacac cctttaagtn aggtgacagg tcacctttaa gtgaggacag tcagctnaat      120
ttcacctctt gggcttgagt acctggttct cgtgccctga ggcgacnctn agccctgcag      180
ctnccatgta cgtgctgcca atngtcttga tcttctccac gccnctnaac ttgggcttca      240
gtaggagctg caggcnagaa ngaagcggtt aacagcgcca ctccatagcc gcagccnggc      300
tgcccctgct tctcaaggag gggtgtgggg ttcctccacc atcgccgccc ttgcaaacac      360
ntctcanggc ttccctnccg gctnancgca ngacttaagc atgg                       404
```

```
<210> SEQ ID NO 17
<211> LENGTH: 360
<212> TYPE: DNA
<213> ORGANISM: Homo sapien
<220> FEATURE:
<221> NAME/KEY: misc_feature
<222> LOCATION: (1)...(360)
<223> OTHER INFORMATION: n = A,T,C or G

<400> SEQUENCE: 17
ggccagaagc tttccacaaa ccagtgaagg tggcagcaaa gaaagcctct tagacnagga       60
gctggcagca gctgctatct ngatngacng cagaaaccaa ccactaattc agcaaacaca      120
acctcatacc tnaccgcttc cctttnaatg gccttcggtg tgtgcgcaca tgggcacgtg      180
```

| | |
|---|---|
| cggggagaac catacttatt ccoctnttcc cggcctacca cctctnctcc cccttctctt | 240 |
| ctctncaatt actntctccn ctgctttntt ctnancacta ctgctngtnt cnanagccng | 300 |
| cccgcaatta cctggcaaaa ctcgcgaccc ttcgggcagc gctaaanaat gcacatttac | 360 |

<210> SEQ ID NO 18
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 18

| | |
|---|---|
| atacatatac acatatatga ttttagatag agccatatac ctngaagtag tanatttgtt | 60 |
| tgtgtgtata tgtatgtgtc tactcatttt aaataaactt gtgatagaga tgtaattntg | 120 |
| agccagtttt tcatttgctt aaatnactca ccaagtaact aattaagttn tctttactct | 180 |
| taatgttnag tagtgagatt ctgttgaagg tgatattaaa aaccattcta tattaattaa | 240 |
| cattcatgtt gttttttaaa agcttatttg aaatcnaatt atgattattt ttcataccag | 300 |
| tcgatnttat gtangt | 316 |

<210> SEQ ID NO 19
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 19

| | |
|---|---|
| aagggatgca nataatgctg tgtatgagct tgatggaaaa gaactctgta gtgaaagggt | 60 |
| tactattgaa catgctnggg ctcggtcacg aggtggaaga ggtagaggac gatactctga | 120 |
| ccgttttagt agtcgcagac ctcgaaatga tagacgaaat gctccacctg taagaacaga | 180 |
| anatcgtctt atagttgaga atttatcctc aagagtcagc tggcaggttt gttganatac | 240 |
| agttttgagt tnttttgatg tggctttta aaaaagttat gggttactna tgttatattg | 300 |
| ttttattaaa agtagttttn aattaatgga tntgatggaa ttgttgtttt | 350 |

<210> SEQ ID NO 20
<211> LENGTH: 367
<212> TYPE: DNA
<213> ORGANISM: Homo sapien
<220> FEATURE:
<221> NAME/KEY: misc_feature
<222> LOCATION: (1)...(367)
<223> OTHER INFORMATION: n = A,T,C or G

<400> SEQUENCE: 20

| | |
|---|---|
| gntnnncnca agatcctnct ntcccccngg gcngcccnc cnccngtnat naccggtttn | 60 |
| ntaanatcnn gccgcncccg aagtctcnct nntgccgaga tgnccttat ncncnnatgn | 120 |
| ncaattntga cctnnggcga anaatggcng nngtgtatca gtntccnctc tgnggnctct | 180 |
| tagnatctga ccactangac ccnctatcct ctcaaccct gtanncngcc ctaatttgtg | 240 |
| ccaattagtg catgntanag cntcctggcc cagatggcnt ccatatcctg gtncggcttc | 300 |
| cgcccctacc angncatccn catctactag agcttatccg ctncntgngg cgcaccggnt | 360 |
| ccccnct | 367 |

<210> SEQ ID NO 21
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 21

| | | | | | |
|---|---|---|---|---|---|
| cccaacacaa | tggtctaagt | anaactgtat | tgctctgtag | tatagttcca | cattggcaac | 60 |
| ctacaatggg | aaaatccata | cataagtcag | ttacttcctn | atgagctttc | tccttctgaa | 120 |
| tcctttatct | tctgaagaaa | gtacacacct | tggtnatgat | atctttgaat | tgcccttctt | 180 |
| tccaggcatc | agttggatga | ttcatcatgg | taattatggc | attatcatat | tcttcatact | 240 |
| tgtcatacga | aaacaccagt | tctgcccnna | gatgagcttg | ttctgcagct | cttagcacct | 300 |
| tgggaatatt | cactctagac | cagaaacagc | tcccggtgct | ccctcatttt | ctgaggctta | 360 |
| aattttn | | | | | | 366 |

<210> SEQ ID NO 22
<211> LENGTH: 315
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 22

| | | | | | |
|---|---|---|---|---|---|
| acttaatgca | atctctggag | gataatttgg | atcaagaaat | aaagaanaaa | tgaattagga | 60 |
| gaagaaatna | ctgggtnata | tttcaatatt | ttagaacttt | aanaatgttg | actatgattt | 120 |
| caatatattt | gtnaaaactg | agatacangt | ttgacctata | tctgcattt | gataattaaa | 180 |
| cnaatnnatt | ctatttnaat | gttgtttcag | agtcacagca | cagactgaaa | cttttttga | 240 |
| atacctnaat | atcacacttn | tncttnnaat | gatgttgaag | acaatgatga | catgccttna | 300 |
| gcatataatg | tcgac | | | | | 315 |

<210> SEQ ID NO 23
<211> LENGTH: 202
<212> TYPE: DNA
<213> ORGANISM: Homo sapien
<220> FEATURE:
<221> NAME/KEY: misc_feature
<222> LOCATION: (1)...(202)
<223> OTHER INFORMATION: n = A,T,C or G

<400> SEQUENCE: 23

| | | | | | |
|---|---|---|---|---|---|
| actaatccag | tgtggtgnaa | ttccattgtg | ttgggcaact | caggatatta | aatttatnat | 60 |
| ttaaaaattc | ccaagagaaa | naaactccag | gccctgattg | tttcactggg | gaattttacc | 120 |
| aaatgttnca | nnaaganatg | acgctgattc | tgtnaaatct | ttttcagaag | atagaggaga | 180 |
| acacccaccg | nttcatttta | tg | | | | 202 |

<210> SEQ ID NO 24
<211> LENGTH: 365
<212> TYPE: DNA
<213> ORGANISM: Homo sapien
<220> FEATURE:
<221> NAME/KEY: misc_feature
<222> LOCATION: (1)...(365)

<223> OTHER INFORMATION: n = A,T,C or G

<400> SEQUENCE: 24

```
ggatttcttg ccctttctc cctttttaag tatcaatgta tgaaatccac ctgtaccacc      60
ctttctgcca tacaaccgct accacatctg gctcctagaa cctgttttgc tttcatagat    120
ggatctcgga accnagtgtt nacttcattt ttaaacccca ttttagcaga tngtttgctn    180
tggtctgtct gtattcacca tggggcctgt acacaccacg tgtggttata gtcaaacaca    240
gtgccctcca ttgtggccac atgggagacc catnacccna tactgcatcc tgggctgatn    300
acggcactgc atctnacccg acntgggatt gaacccgggg tgggcagcng aattgaacag    360
gatca                                                                365
```

<210> SEQ ID NO 25
<211> LENGTH: 359
<212> TYPE: DNA
<213> ORGANISM: Homo sapien
<220> FEATURE:
<221> NAME/KEY: misc_feature
<222> LOCATION: (1)...(359)
<223> OTHER INFORMATION: n = A,T,C or G

<400> SEQUENCE: 25

```
gtttcctgct tcaacagtgc ttggacggaa cccggcgctc gttccccacc ccggccggcc     60
gcccatagcc agccctccgt cacctcttca ccgcaccctc ggactgcccc aaggcccccg    120
ccgccnctcc ngcgccncgc agccaccgcc gccnccncca cctctccttn gtcccgccnt    180
nacaacgcgt ccacctcgca ngttcgccng aactaccacc nggactcata ngccgccctc    240
aaccgcccga tcaacctgga gctctncccc ccgacnttaa cctttccntg tcttacttac    300
nttaaccgcc gnttattttg cttnaaaaga acttttcccc aatactttct ttcaccnnt     359
```

<210> SEQ ID NO 26
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 26

```
agtgaaacag tatatgtgaa aaggagtttg tgannagcta cataaaaata ttagatatct     60
ttataatttc caataggata ctcatcagtt ttgaataana gacatattct agagaaacca    120
ggtttctggt ttcagatttg aactctcaag agcttggaag ttatcactcc catcctcacg    180
acnacnaana aatctnaacn aacngaaanac caatgacttt tcttagatct gtcaaagaac    240
ttcagccacg aggaaaacta tcnccctnaa tactggggac tggaaagaga gggtacagag    300
aatcacagtg aatcatagcc caagatcagc ttgcccggag ctnaagctng tacgatnatt    360
acttacaggg accacttcac agtnngtnga tnaantgccn                          400
```

<210> SEQ ID NO 27
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 27

```
gaatttctta gaaactgaag tttactctgt tccaagatat atcttcactg tcttaatcaa      60
agggcgctng aatcatagca aatattctca tctttcaact aactttaagt agttntcctg     120
gaattttaca ttttccagaa aacactcctt tctgtatctg tgaaagaaag tgtgcctcag     180
gctgtagact gggctgcact ggacacctgc gggggactct ggctnagtgn ggacatggtc     240
agtattgatt ttcctcanac tcagcctgtg tagctntgaa agcatggaac agattacact     300
gcagttnacg tcatcccaca catcttggac tccnagaccc ggggaggtca catagtccgt     360 tatgna                                                                366

<210> SEQ ID NO 28
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 28
agtgggagcc tcctccttcc ccactcagtt ctttacatcc ccgaggcgca gctgggcnaa      60
ggaagtggcc agctgcagcg cctcctgcag gcagccaacg ttcttgcctg tggcctgtgc     120
agacacatcc ttgccaccac ctttaccgtc catcangcct gacacctgct gcacccactc     180
gctngctttt aagccccgat nggctgcatt ctgggggact tgacacaggc ncgtgatctt     240
gccagcctca ttgtccaccg tgaagagcat ggcaaaaagt ctgaggggag tgcatcttga     300
anagcttcaa ggcttcattc agggcctttng ctnaggcgcc nctctccatc tccnggaata     360
acnagaggct ggtnngggtn actntcaata aactgcttcg tc                        402

<210> SEQ ID NO 29
<211> LENGTH: 175
<212> TYPE: DNA
<213> ORGANISM: Homo sapien

<400> SEQUENCE: 29
cggacgggca tgaccggtcc ggtcagctgg gtggccagtt tcagttcttc agcagaactg      60
tctcccttct tggggccga ggcttcctg gggaagagga tgagtttgga gcggtactcc     120
ttcagccgct gcacgttggt ctgcagggac tccgtggact tgttccgcct cctcg          175

<210> SEQ ID NO 30
<211> LENGTH: 360
<212> TYPE: DNA
<213> ORGANISM: Homo sapien

<400> SEQUENCE: 30
ttgtatttct tatgatctct gatgggttct tctcgaaaat gccaagtgga agactttgtg      60
gcatgctcca gatttaaatc cagctgaggc tccctttgtt ttcagttcca tgtaacaatc     120
tggaaggaaa cttcacggac aggaagactg ctggagaaga gaagcgtgtt agcccatttg     180
aggtctgggg aatcatgtaa agggtaccca gacctcactt ttagttattt acatcaatga     240
gttctttcag ggaaccaaac ccagaattcg gtgcaaaagc caaacatctt ggtgggattt     300
gataaatgcc ttgggacctg gagtgctggg cttgtgcaca ggaagagcac cagccgctga     360

<210> SEQ ID NO 31
<211> LENGTH: 380
<212> TYPE: DNA
```

<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 31

| | | | | | |
|---|---|---|---|---|---|
| acgctctaag | cctgtccacg | agctcaatag | ggaagcctgt | gatgactaca | gactttgcga | 60 |
| acgctacgcc | atggtttatg | gatacaatgc | tgcctataan | cgctacttca | ggaagcgccg | 120 |
| agggaccnaa | tgagactgag | ggaagaaaaa | aaatctcttt | ttttctggag | gctggcacct | 180 |
| gattttgtat | ccccctgtnn | cagcattncn | gaaatacata | ggcttatata | caatgcttct | 240 |
| ttcctgtata | ttctcttgtc | tggctgcacc | ccttnttccc | gccccagat | tgataagtaa | 300 |
| tgaaagtgca | ctgcagtnag | ggtcaangga | gactcancat | atgtgattgt | tccntnataa | 360 |
| acttctggtg | tgatactttc | | | | | 380 |

<210> SEQ ID NO 32
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 32

| | | | | | |
|---|---|---|---|---|---|
| gtgtatggga | gcccctgact | cctcacgtgc | ctgatctgtg | cccttggtcc | caggtcaggc | 60 |
| ccaccccctg | cacctccacc | tgccccagcc | cctgcctctg | ccccaagtgg | ggccagctgc | 120 |
| cctcacttct | ggggtggatg | atgtgacctt | cctnggggga | ctgcggaagg | gacaagggtt | 180 |
| ccctgaagtc | ttacggtcca | acatcaggac | caagtcccat | ggacatgctg | acagggtccc | 240 |
| caggggagac | cgtntcanta | gggatgtgtg | cctggctgtg | tacgtgggtg | tgcagtgcac | 300 |
| gtganaagca | cgtggcggct | tctgggggcc | atgtttgggg | aaggaagtgt | gcccnccacc | 360 |
| cttggagaac | ctcagtcccn | gtagccccct | gccctggcac | agcngcatnc | acttcaaggg | 420 |
| caccctttgg | gggttgggt | | | | | 440 |

<210> SEQ ID NO 33
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 33

| | | | | | |
|---|---|---|---|---|---|
| tattttaaca | atgtttatta | ttcatttatc | cctctataga | accaccaccc | acaccgagga | 60 |
| gattatttgg | agtgggtccc | aacctagggc | ctggactctg | aaatctaact | ccccacttcc | 120 |
| ctcattttgt | gacttaggtg | ggggcatggt | tcagtcagaa | ctggtgtctc | ctattggatc | 180 |
| gtgcagaagg | aggacctagg | cacacacata | tggtggccac | acccaggagg | gttgattggc | 240 |
| aggctggaag | acaaaagtct | cccaataaag | gcacttttac | ctcaaagang | gggtgggagt | 300 |
| tggtctgctg | ggaatgttgt | tgttggggtg | gggaagantt | atttc | | 345 |

<210> SEQ ID NO 34
<211> LENGTH: 440
<212> TYPE: DNA
<213> ORGANISM: Homo sapien

```
<220> FEATURE:
<221> NAME/KEY: misc_feature
<222> LOCATION: (1)...(440)
<223> OTHER INFORMATION: n = A,T,C or G

<400> SEQUENCE: 34
tgtaattttt ttattggaaa acaaatatac aacttggaat ggattttgag gcaaattgtg      60
ccataagcag attttaagtg gctaaacaaa gtttaaaaag caagtaacaa taaaagaaaa     120
tgtttctggt acaggaccag cagtacaaaa aaatagtgta cgagtacctg gataatacac     180
ccgttttgca atagtgcaac ttttaagtac atattgttga ctgtccatag tccacgcaga     240
gttacaactc cacacttcaa caacaacatg ctgacagttc ctaaagaaaa ctactttaaa     300
aaaggcataa cccagatgtt ccctcatttg accaactcca tctnagttta gatgtgcaga     360
agggcttana ttttcccaga gtaagccnca tgcaacatgt tacttgatca attttctaaa     420
ataaggtttt aggacaatga                                                 440

<210> SEQ ID NO 35
<211> LENGTH: 540
<212> TYPE: DNA
<213> ORGANISM: Homo sapien
<220> FEATURE:
<221> NAME/KEY: misc_feature
<222> LOCATION: (1)...(540)
<223> OTHER INFORMATION: n = A,T,C or G

<400> SEQUENCE: 35
atagatggaa tttattaagc ttttcacatg tgatagcaca tagttttaat tgcatccaaa      60
gtactaacaa aaactctagc aatcaagaat ggcagcatgt tattttataa caatcaacac     120
ctgtggcttt taaaatttgg ttttcataag ataatttata ctgaagtaaa tctagccatg     180
cttttaaaaa atgctttagg tcactccaag cttggcagtt aacatttggc ataaacaata     240 ataaacaat cacaatttaa taaataacaa atacaacatt gtaggccata atcatataca      300
gtataaggga aaaggtggta gtgttganta agcagttatt agaatagaat accttggcct     360
ctatgcaaat atgtctagac actttgattc actcagccct gacattcagt tttcaaagtt     420
aggaaacagg ttctacagta tcattttaca gtttccaaca cattgaaaac aagtagaaaa     480
tgatganttg attttttatta atgcattaca tcctcaagan ttatcaccaa cccctcaggt     540

<210> SEQ ID NO 36
<211> LENGTH: 555
<212> TYPE: DNA
<213> ORGANISM: Homo sapien
<220> FEATURE:
<221> NAME/KEY: misc_feature
<222> LOCATION: (1)...(555)
<223> OTHER INFORMATION: n = A,T,C or G

<400> SEQUENCE: 36
cttcgtgtgc ttgaaaattg gagcctgccc ctcggcccat aagcccttgt tgggaactga      60
gaagtgtata tgggcccaa nctactggtg ccagaacaca gagacagcag cccantgcaa     120
tgctgtcgag cattgcaaac gccatgtgtg gaactaggag gaggaatatt ccatcttggc     180
agaaaccaca gcattggttt ttttctactt gtgtgtctgg gggaatgaac gcacagatct     240
gtttgacttt gttataaaaa tagggctccc ccacctcccc cntttctgtg tncttttattg     300 tagcantgct gtctgcaagg gagccccta ncccctgcag acananctgc ttcagtgccc     360 cttttcctctc tgctaaatgg atgttgatgc actggaggtc ttttanccctg cccttgcatg     420
```

```
gcncctgctg gaggaagana aaactctgct ggcatgaccc acagtttctt gactggangc      480
cntcaaccct cttggttgaa gccttgttct gaccctgaca tntgcttggg cnctgggtng      540
gnctgggctt ctnaa                                                       555

<210> SEQ ID NO 37
<211> LENGTH: 280
<212> TYPE: DNA
<213> ORGANISM: Homo sapien
<220> FEATURE:
<221> NAME/KEY: misc_feature
<222> LOCATION: (1)...(280)
<223> OTHER INFORMATION: n = A,T,C or G

<400> SEQUENCE: 37
ccaccgacta taagaactat gccctcgtgt attcctgtac ctgcatcatc caactttttc       60
acgtggattt tgcttggatc ttggcaagaa accctaatct ccctccagaa acagtggact      120
ctctaaaaaa tatcctgact tctaataaca ttgatntcaa gaaaatgacg gtcacagacc      180
aggtgaactg ccccnagctc tcgtaaccag gttctacagg gaggctgcac ccactccatg      240
ttncttctgc ttcgctttcc cctaccccac ccccgccat                             280

<210> SEQ ID NO 38
<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 38
catcgagctg gttgtcttct tgcctgccct gtgtcgtaaa atgggggtcc cttactgcat       60
tatcaaggga aaggcaagac tgggacgtct agtccacagg aagacctgca ccactgtcgc      120
cttcacacag gtgaactcgg aagacaaagg cgctttggct nagctggtgn aagctatcag      180
gaccaattac aatgacngat acgatnagat ccgccntcac tggggtagca atgtcctggg      240
tcctaagtct gtggctcgta tcgccnagct cgaanaggcn aangctaaag aacttgccac      300
taa                                                                    303

<210> SEQ ID NO 39
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 39
gactcagcgg ctggtgctct tcctgtgcac aagcccagca ctccaggtcc caaggcattt       60
atcaaatccc accaagatnt ttggcttttg caccgaattc tgggtttggt tccctnaaag      120
aactcattga tgtaaatnac tnaaagtgag gtctgggtac cctttacatg attccccaga      180
cctcanatgg gctaacacgc ttctcttctc cagcagtctt cctntccgtg aagttacctt      240
ccagattgtt acatggaact gaanacaaag ggagcctcag ctngatttaa atctggagca      300

<210> SEQ ID NO 40
<211> LENGTH: 318
<212> TYPE: DNA
<213> ORGANISM: Homo sapien
```

<220> FEATURE:
<221> NAME/KEY: misc_feature
<222> LOCATION: (1)...(318)
<223> OTHER INFORMATION: n = A,T,C or G

<400> SEQUENCE: 40

| | | | | | |
|---|---|---|---|---|---|
| cccaacacaa | tggctgagga | caaatcagtt | ctctgtgacc | agacatgaga | aggttgccaa | 60 |
| tgggctgttg | ggcgaccaag | gccttcccgg | agtcttcgtc | ctctatgagc | tctcgcccat | 120 |
| gatggtgaag | ctgacggaga | agcacaggtc | cttcacccac | ttcctgacag | gtgtgtgcgc | 180 |
| catcattggg | ggcatgttca | cagtggctgg | actcatcgat | tcgctcatct | accactcagc | 240 |
| acgagccatc | cagaaaaaaa | ttgatctngg | gaagacnacg | tagtcaccct | cggtncttcc | 300 |
| tctgtctcct | ctttctcc | | | | | 318 |

<210> SEQ ID NO 41
<211> LENGTH: 302
<212> TYPE: DNA
<213> ORGANISM: Homo sapien
<220> FEATURE:
<221> NAME/KEY: misc_feature
<222> LOCATION: (1)...(302)
<223> OTHER INFORMATION: n = A,T,C or G

<400> SEQUENCE: 41

| | | | | | |
|---|---|---|---|---|---|
| acttagatgg | ggtccgttca | ggggatacca | gcgttcacat | ttttcctttt | aagaaagggt | 60 |
| cttggcctga | atgttcccca | tccggacaca | ggctgcatgt | ctctgtnagt | gtcaaagctg | 120 |
| ccatnaccat | ctcggtaacc | tactcttact | ccacaatgtc | tatnttcact | gcagggctct | 180 |
| ataatnagtc | cataatgtaa | atgcctggcc | caagacntat | ggcctgagtt | tatccnaggc | 240 |
| ccaaacnatt | accagacatt | cctcttanat | tgaaaacgga | tntctttccc | ttggcaaaga | 300 |
| tc | | | | | | 302 |

<210> SEQ ID NO 42
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 42

| | | | | | |
|---|---|---|---|---|---|
| cttaataagt | ttaaggccaa | ggcccgttcc | attcttctag | caactgacgt | tgccagccga | 60 |
| ggtttggaca | tacctcatgt | aaatgtggtt | gtcaactttg | acattcctac | ccattccaag | 120 |
| gattacatcc | atcgagtagg | tcgaacagct | agagctgggc | gctccggaaa | ggctattact | 180 |
| tttgtcacac | agtatgatgt | ggaactcttc | cagcgcatag | aacacttnat | tgggaagaaa | 240 |
| ctaccaggtt | ttccaacaca | ggatgatgag | gttatgatgc | tnacggaacg | cgtcgctna | 299 |

<210> SEQ ID NO 43
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 43

| | | | | | |
|---|---|---|---|---|---|
| ccaacaatgt | caagacagcc | gtctgtgaca | tcccacctcg | tggcctcaan | atggcagtca | 60 |

-continued

| | |
|---|---|
| ccttcattgg caatagcaca gccntccggg agctcttcaa gcgcatctcg gagcagttca | 120 |
| ctgccatgtt ccgccggaag gccttcctcc actggtacac aggcgagggc atggacaaga | 180 |
| tggagttcac cgaggctgag agcaacatga acgacctcgt ctctnagtat cagcagtacc | 240 |
| gggatgccac cgcagaaana ggaggaggat ttcggtnagg aggccgaaga aggaggcctg | 300 |
| aggca | 305 |

<210> SEQ ID NO 44
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 44

| | |
|---|---|
| tttctgtggg ggaaacctga tctcgacnaa attagagaat tttgtcagcg gtatttcggc | 60 |
| tggaacagaa cgaaaacnga tnaatctctg tttcctgtat aaagcaact cgatncccag | 120 |
| cagacacagc tccnaattga ttccttcttt ngattagcac aacagggaga agaanatgc | 180 |
| ttaacgtatt aagagccnga gactaaacag agctttgaca tgtatgctta ggaaagagaa | 240 |
| agaagcagcn gcccgcgnaa ttngaagcng tttctgttgc cntgganaaa gaatttgagc | 300 |
| ttctttatta ggccaacgaa aaccccgaa ananaggcnt tacnatacct tngaaaantc | 360 |
| tccngccnna aaaagaaaga agctttcnga ttcttaacc | 399 |

<210> SEQ ID NO 45
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 45

| | |
|---|---|
| gcgggagcag aagctaaagc caaagcccaa gagagtggca gtgccagcac tggtgccagt | 60 |
| accagtacca ataacagtgc cagtgccagt gccagcacca gtggtggctt cagtgctggt | 120 |
| gccagcctga ccgccactct cacatttggg ctcttcgctg gccttggtgg agctggtgcc | 180 |
| agcaccagtg gcagctctgg tgcctgtggt ttctcctaca agtgagattt taggtatctg | 240 |
| ccttggttc agtggggaca tctggggctt angggggcngg gataaggagc tggatgattc | 300 |
| taggaaggcc cangttggag aangatgtgn anagtgtgcc aagacactgc ttttggcatt | 360 |
| ttattccttt ctgtttgctg gangtcaatt gacccttnna ntttctctta cttgtgtttt | 420 |
| canatatngt taatcctgcc | 440 |

<210> SEQ ID NO 46
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 46

| | |
|---|---|
| gctctgtaat ttcacatttt aaaccttccc ttgacctcac attcctcttc ggccacctct | 60 |
| gtttctctgt tcctcttcac agcaaaaact gttcaaaaga gttgttgatt actttcattt | 120 |

```
ccactttctc accccccattc tcccctcaat taactctcct tcatccccat gatgccatta      180
tgtggctntt attanagtca ccaaccttat tctccaaaac anaagcaaca aggactttga      240
cttctcagca gcactcagct ctggtncttg aaacacccccc gttacttgct attcctccta     300
cctcataaca atctccttcc cagcctctac tgctgccttc tctgagttct tcccagggtc      360
ctaggctcag atgtagtgta gctcaaccct gctacacaaa gnaatctcct gaaagcctgt     420
aaaaatgtcc atncntgtcc tgtgagtgat ctnccangna naataacaaa tt               472
```

<210> SEQ ID NO 47
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G

<400> SEQUENCE: 47

```
ccttcctccg cctggccatc cccagcatgc tcatgctgtg catggagtgg tgggcctatg       60
aggtcgggag cttcctcagt ggtctgtatg aggatggatg acggggactg gtgggaacct      120
gggggccctg tctgggtgca aggcgacagc tgtctttctt caccaggcat cctcggcatg      180
gtggagctgg gcgctcagtc catcgtgtat gaactggcca tcattgtgta catggtccct      240
gcaggcttca gtgtggctgc cagtgtccgg gtangaaacg ctctgggtgc tggagacatg      300
gaagcaggca cggaagtcct ctaccgtttc cctgctgatt acagtgctct tgctgtanc       360 cttcagtgtc ctgctgttaa gctgtaagga tcacntgggg tacattttta ctaccgaccg      420
agaacatcat taatctggtg gctcaggtgg ttccaattta tgctgtttcc cacctctttg     480
aagctcttgc tgctcaggta cacgccaatt ttgaaaagta acaacgtgc ctcggagtgg       540 gaattctgct                                                             550
```

<210> SEQ ID NO 48
<211> LENGTH: 214
<212> TYPE: DNA
<213> ORGANISM: Homo sapien
<220> FEATURE:
<221> NAME/KEY: misc_feature
<222> LOCATION: (1)...(214)
<223> OTHER INFORMATION: n = A,T,C or G

<400> SEQUENCE: 48

```
agaaggacat aaacaagctg aacctgccca agacgtgtga tatcagcttc tcagatccag       60
acaacctcct caacttcaag ctggtcatct gtcctgatna gggcttctac nagagtggga     120
agtttgtgtt cagttttaag gtgggccagg gttacccgca tgatcccccc aaggtgaagt      180
gtgagacnat ggtctatcac cccnacattg acct                                  214
```

<210> SEQ ID NO 49
<211> LENGTH: 267
<212> TYPE: DNA
<213> ORGANISM: Homo sapien
<220> FEATURE:
<221> NAME/KEY: misc_feature
<222> LOCATION: (1)...(267)
<223> OTHER INFORMATION: n = A,T,C or G

<400> SEQUENCE: 49

```
atctgcctaa aatttattca aataatgaaa atnaatctgt tttaagaaat tcagtctttt       60
```

```
agtttttagg acaactatgc acaaatgtac gatggagaat tcttttttgga tnaactctag    120 gtngaggaac ttaatccaac cggagctntt gtgaaggtca gaaacagga gagggaatct     180 tggcaaggaa tggagacnga gtttgcaaat tgcagctaga gtnaatngtt ntaaatggga   240
ctgctnttgt gtctcccang gaaagtt                                         267
```

<210> SEQ ID NO 50
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 50

```
gactgggtca aagctgcatg aaaccaggcc ctggcagcaa cctgggaatg gctggaggtg    60
ggagagaacc tgacttctct ttccctctcc ctcctccaac attactggaa ctctgtcctg   120
ttgggatctt ctgagcttgt ttccctgctg ggtgggacag aggacaaagg agaagggagg   180
gtctagaaga ggcagccctt ctttgtcctc tggggtnaat gagcttgacc tanagtagat   240
ggagagacca anagcctctg attttaatt tccataanat gttcnaagta tatntntacc    300
```

<210> SEQ ID NO 51
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 51

```
gggtaaaatc ctgcagcacc cactctggaa aatactgctc ttaattttcc tgaaggtggc    60
cccctatttc tagttggtcc aggattaggg atgtgggta tagggcattt aaatcctctc   120
aagcgctctc caagcacccc cggcctgggg gtnagtttct catcccgcta ctgctgctgg   180
gatcaggttn aataaatgga actcttcctg tctggcctcc aaagcagcct aaaaactgag   240
gggctctgtt agaggggacc tccaccctnn ggaagtccga ggggctnggg aagggtttct   300
```

<210> SEQ ID NO 52
<211> LENGTH: 267
<212> TYPE: DNA
<213> ORGANISM: Homo sapien
<220> FEATURE:
<221> NAME/KEY: misc_feature
<222> LOCATION: (1)...(267)
<223> OTHER INFORMATION: n = A,T,C or G

<400> SEQUENCE: 52

```
aaaatcaact tcntgcatta atanacanat tctanancag gaagtgaana taattttctg   60
cacctatcaa ggaacnnact tgattgcctc tattnaacan atatatcgag ttnctatact   120
tacctgaata ccnccgcata actctcaacc nanatncntc nccatgacac tcnttcttna   180
atgctantcc cgaattcttc attatatcng tgatgttcgn cctgntnata tatcagcaag   240
gtatgtnccn taactgccga nncaang                                         267
```

<210> SEQ ID NO 53
<211> LENGTH: 401
<212> TYPE: DNA
<213> ORGANISM: Homo sapien

<400> SEQUENCE: 53

```
agsctttagc atcatgtaga agcaaactgc acctatggct gagataggtg caatgaccta      60
caagattttg tgttttctag ctgtccagga aaagccatct tcagtcttgc tgacagtcaa     120
agagcaagtg aaaccatttc cagcctaaac tacataaaag cagccgaacc aatgattaaa     180
gacctctaag gctccataat catcattaaa tatgcccaaa ctcattgtga cttttttattt    240
tatatacagg attaaaatca acattaaatc atcttattta catggccatc ggtgctgaaa     300
ttgagcattt taaatagtac agtaggctgg tatacattag gaaatggact gcactggagg     360
caaatagaaa actaaagaaa ttagataggc tggaaatgct t                         401
```

<210> SEQ ID NO 54
<211> LENGTH: 401
<212> TYPE: DNA
<213> ORGANISM: Homo sapien

<400> SEQUENCE: 54

```
cccaacacaa tggataaaaa cacttatagt aaatggggac attcactata atgatctaag      60
aagctacaga ttgtcatagt tgttttcctg ctttacaaaa ttgctccaga tctggaatgc     120
cagtttgacc tttgtcttct ataatatttc ctttttttcc cctctttgaa tctctgtata     180
tttgattctt aactaaaatt gttctcttaa atattctgaa tcctggtaat taaaagtttg     240
ggtgtatttt ctttacctcc aaggaaagaa ctactagcta caaaaaatat tttggaataa     300
gcattgtttt ggtataaggt acatattttg gttgaagaca ccagactgaa gtaaacagct     360
gtgcatccaa tttattatag ttttgtaagt aacaatatgt a                         401
```

<210> SEQ ID NO 55
<211> LENGTH: 933
<212> TYPE: DNA
<213> ORGANISM: Homo sapien

<400> SEQUENCE: 55

```
tttactgctt ggcaaagtac cctgagcatc agcagagatg ccgagatgaa atcagggaac      60
tcctagggga tgggtcttct attacctggg aacacctgag ccagatgcct acaccacga      120
tgtgcatcaa ggaatgcctc cgcctctacg caccggtagt aaactatccc ggttactcga     180
caaacccatc accttttccag atggacgctc cttacctgca ggaataactg tgtttatcaa     240
tatttgggct cttcaccaca acccctattt ctgggaagac cctcaggtct ttaacccctt     300
gagattctcc aggaaaaatt ctgaaaaaat acatccctat gccttcatac cattctcagc     360
tggattaagg aactgcattg gcagcatttt gccataatt gagtgtaaag tggcagtggc      420
attaactctg ctccgcttca agctggctcc agaccactca aggccaccca gctgtcgtca     480
agttgcctca agtccaagaa tggaatccat gtgtttgcaa aaaaagtttg ctaattttaa     540
gtccttttcg tataagaatt aakgagacaa ttttcctacc aaaggaagaa caaaaggata     600
aatataatac aaaatatatg tatatggttg tttgacaaat tatataactt aggatacttc     660
tgactggttt tgcatccat taacagtaat tttaatttct ttgctgtatc tggtgaaacc     720
cacaaaaaca cctgaaaaaa ctcaagctga gttccaatgc gaagggaaat gattggtttg     780
ggtaactagt ggtagagtgg ctttcaagca tagtttgatc aaaactccac tcagtatctg     840
cattacttt atctctgcaa atatctgcat gatagcttta ttctcagtta tctttcccca     900
taataaaaaa tatctgccaa aaaaaaaaaa aaa                                   933
```

<210> SEQ ID NO 56
<211> LENGTH: 480
<212> TYPE: DNA
<213> ORGANISM: Homo sapien

<400> SEQUENCE: 56

| | | | | | |
|---|---|---|---|---|---|
| ggctttgaag | cattttttgtc | tgtgctccct | gatcttcagg | tcaccaccat | gaagttctta | 60 |
| gcagtcctgg | tactcttggg | agtttccatc | tttctggtct | ctgcccagaa | tccgacaaca | 120 |
| gctgctccag | ctgacacgta | tccagctact | ggtcctgctg | atgatgaagc | ccctgatgct | 180 |
| gaaaccactg | ctgctgcaac | cactgcgacc | actgctgctc | ctaccactgc | aaccaccgct | 240 |
| gcttctacca | ctgctcgtaa | agacattcca | gttttaccca | aatgggttgg | ggatctcccg | 300 |
| aatggtagag | tgtgtccctg | agatggaatc | agcttgagtc | ttctgcaatt | ggtcacaact | 360 |
| attcatgctt | cctgtgattt | catccaacta | cttaccttgc | ctacgatatc | cccttttatct | 420 |
| ctaatcagtt | tattttctttt | caaataaaaa | ataactatga | gcaacaaaaa | aaaaaaaaaa | 480 |

<210> SEQ ID NO 57
<211> LENGTH: 798
<212> TYPE: DNA
<213> ORGANISM: Homo sapien

<400> SEQUENCE: 57

| | | | | | |
|---|---|---|---|---|---|
| agcctacctg | gaaagccaac | cagtcctcat | aatggacaag | atccaccagc | tcctcctgtg | 60 |
| gactaacttt | gtgatatggg | aagtgaaaat | agttaacacc | ttgcacgacc | aaacgaacga | 120 |
| agatgaccag | agtactctta | accccttaga | actgttttttc | cttttgtatc | tgcaatatgg | 180 |
| gatggtattg | ttttcatgag | cttctagaaa | tttcacttgc | aagtttattt | ttgcttcctg | 240 |
| tgttactgcc | attcctatttt | acagtatatt | tgagtgaatg | attatatttt | taaaaagtta | 300 |
| catgggctt | ttttggttgt | cctaaactta | caaacattcc | actcattctg | tttgtaactg | 360 |
| tgattataat | ttttgtgata | atttctggcc | tgattgaagg | aaatttgaga | ggtctgcatt | 420 |
| tatatatttt | aaatagattt | gataggtttt | taaattgctt | tttttcataa | ggtatttata | 480 |
| aagttatttg | gggttgtctg | ggattgtgtg | aaagaaaatt | agaacccgc | tgtatttaca | 540 |
| tttaccttgg | tagtttatttt | gtggatggca | gttttctgta | gttttgggga | ctgtggtagc | 600 |
| tcttggattg | ttttgcaaat | tacagctgaa | atctgtgtca | tggattaaac | tggcttatgt | 660 |
| ggctagaata | ggaagagaga | aaaatgaaa | tggttgttta | ctaattttat | actcccatta | 720 |
| aaaattttta | atgttaagaa | aaccttaaat | aaacatgatt | gatcaatatg | gaaaaaaaaa | 780 |
| aaaaaaaaaa | aaaaaaaa | | | | | 798 |

<210> SEQ ID NO 58
<211> LENGTH: 280
<212> TYPE: DNA
<213> ORGANISM: Homo sapien

<400> SEQUENCE: 58

| | | | | | |
|---|---|---|---|---|---|
| ggggcagctc | ctgaccctcc | acagccacct | ggtcagccac | cagctggggc | aacgagggtg | 60 |
| gaggtcccac | tgagcctctc | gcctgccccc | gccactcgtc | tggtgcttgt | tgatccaagt | 120 |
| cccctgcctg | gtcccccaca | aggactccca | tccaggcccc | ctctgccctg | ccccttgtca | 180 |
| tggaccatgg | tcgtgaggaa | gggctcatgc | cccttattta | tgggaaccat | ttcattctaa | 240 |
| cagaataaac | cgagaaggaa | accagaaaaa | aaaaaaaaaa | | | 280 |

<210> SEQ ID NO 59
<211> LENGTH: 382
<212> TYPE: DNA
<213> ORGANISM: Homo sapien

<400> SEQUENCE: 59

| | | | | | |
|---|---|---|---|---|---|
| aggcgggagc | agaagctaaa | gccaaagccc | aagagagtgg | cagtgccagc | actggtgcca | 60 |
| gtaccagtac | caataacagt | gccagtgcca | gtgccagcac | cagtggtggc | ttcagtgctg | 120 |
| gtgccagcct | gaccgccact | ctcacatttg | ggctcttcgc | tggccttggt | ggagctggtg | 180 |
| ccagcaccag | tggcagctct | ggtgcctgtg | gtttctccta | caagtgagat | tttagatatt | 240 |
| gttaatcctg | ccagtctttc | tcttcaagcc | agggtgcatc | ctcagaaacc | tactcaacac | 300 |
| agcactctag | gcagccacta | tcaatcaatt | gaagttgaca | ctctgcatta | aatctatttg | 360 |
| ccattaaaaa | aaaaaaaaaa | aa | | | | 382 |

<210> SEQ ID NO 60
<211> LENGTH: 602
<212> TYPE: DNA
<213> ORGANISM: Homo sapien

<400> SEQUENCE: 60

| | | | | | |
|---|---|---|---|---|---|
| tgaagagccg | cgcggtggag | ctgctgcccg | atgggactgc | caaccttgcc | aagctgcagc | 60 |
| ttgtggtgga | gaatagtgcc | cagcgggtca | tccacttggc | gggtcagtgg | gagaagcacc | 120 |
| gggtcccatc | ctcgtgagta | ccgccactcc | gaaagctgca | ggattgcaga | gagctggaat | 180 |
| cttctcgacg | gctggcagag | atccaagaac | tgcaccagag | tgtccgggcg | gctgctgaag | 240 |
| aggcccgcag | gaaggaggag | gtctataagc | agctgatgtc | agagctggag | actctgccca | 300 |
| gagatgtgtc | ccggctggcc | tacacccagc | gcatcctgga | gatcgtgggc | aacatccgga | 360 |
| agcagaagga | agagatcacc | aagatcttgt | ctgatacgaa | ggagcttcag | aaggaaatca | 420 |
| actccctatc | tgggaagctg | gaccggacgt | tgcggtgac | tgatgagctt | gtgttcaagg | 480 |
| atgccaagaa | ggacgatgct | gttcggaagg | cctataagta | tctagctgct | ctgcacgaga | 540 |
| actgcagcca | gctcatccag | accatcgagg | acacaggcac | catcatgcgg | gaggttcgag | 600 |
| ac | | | | | | 602 |

<210> SEQ ID NO 61
<211> LENGTH: 1368
<212> TYPE: DNA
<213> ORGANISM: Homo sapien
<220> FEATURE:
<221> NAME/KEY: misc_feature
<222> LOCATION: (1)...(1368)
<223> OTHER INFORMATION: n = A,T,C or G

<400> SEQUENCE: 61

| | | | | | |
|---|---|---|---|---|---|
| ccagtgagcg | cgcgtaatac | gactcactat | agggcgaatt | gggtaccggg | cccccctcg | 60 |
| agcggccgcc | cttttttttt | tttttttatt | gatcagaatt | caggctttat | tattgagcaa | 120 |
| tgaaaacagc | taaaacttaa | ttccaagcat | gtgtagttaa | agtttgcaaa | gtgggatatt | 180 |
| gttcacaaaa | cacattcaat | gtttaaacac | tatttatttg | aagaacaaaa | tatatttaaa | 240 |
| attgtttgct | tctaaaaagc | ccatttccct | ccaagtctaa | actttgtaat | ttgatattaa | 300 |
| gcaatgaagt | tattttgtac | aatctagtta | aacaagcaga | atagcactag | gcagaataaa | 360 |
| aaattgcaca | gacgtatgca | attttccaag | atagcattct | ttaaattcag | ttttcagctt | 420 |
| ccaaagattg | gttgcccata | atagacttaa | acatataatg | atggctaaaa | aaaataagta | 480 |

```
tacgaaaatg taaaaaagga aatgtaagtc cactctcaat ctcataaaag gtgagagtaa      540
ggatgctaaa gcaaaataaa tgtaggttct ttttttctgt ttccgtttat catgcaatct      600
gcttctttga tatgccttag ggttacccat ttaagttaga ggttgtaatg caatggtggg      660
aatgaaaatt gatcaaatat acaccttgtc atttcatttc aaattgcggg ctggaaactt      720
ccaaaaaaag ggtaggcatg aagaaaaaaa aaatcmaatc agaacctctt caggggtttg      780
kgktctgata tggcagacar gatacaagtc ccaccaggag atggagcaat tcaaaataag      840
ggtaatgggc tgacaaggta ttattgccag catgggacag aatgagcaac aggctgaaaa      900 gttttttggat tatatagcac ctagagtctc tgatgtaggg aattttttgtt agtcaaacat      960 acgctaaact tccaagggaa aatctttcag gtagcctaag cttgcttttc tagagtgatg     1020
agttgcattg ctactgtgat tttttgaaaa caaactgggt ttgtacaagt gagaaagact     1080
agagagaaag attttagtct gtttagcaga agccatttta tctgcgtgca catggatcaa     1140
tatttctgat cccctatacc ccaggaaggg caaaatccca agaaatgtg ttagcaaaat     1200 tggctgatgc tatcatattg ctatggacat tgatcttgcc caacacaatg gaattccacc     1260
acactggact agtggatcca ctagttctag agcggccggc caccgcggtg gagctccagc     1320
ttttgttccc tttagtgagg gttaattgcg cgcttggcgt aatcatnn                  1368

<210> SEQ ID NO 62
<211> LENGTH: 924
<212> TYPE: DNA
<213> ORGANISM: Homo sapien
<220> FEATURE:
<221> NAME/KEY: misc_feature
<222> LOCATION: (1)...(924)
<223> OTHER INFORMATION: n = A,T,C or G

<400> SEQUENCE: 62
caaaggnaca ggaacagctt gnaaagtact gncatncctn cctgcaggga ccagcccttt       60
gcctccaaaa gcaataggaa atttaaaaga tttncactga gaaggggncc acgtttnart      120
tntnaatgtn tcargnanar tnccttncaa atgncrnctn cactnactnr gnatttgggt      180
tnccgnrtnc mgnactatnt caggtttgaa aaactggatc tgccacttat cagttatgtg      240
accttaaaga actccgttaa tttctcagag cctcagtttc cttgtctata agttgggagt      300
aatattaata ctatcatttt tccaaggatt gatgtgaaca ttaatgaggt gaaatgacag      360
atgtgtatca tggttcctaa taaacatcca aaatatagta cttactattg tcattattat      420
tacttgtttg aagctaaaga cctcacaata gaatcccatc cagcccacca gacagagytc      480
tgagttttct agtttggaag agctattaaa taacaacktc tagtgtcaat tctatacttg      540
ttatggtcaa gtaactgggc tcagcatttt acattcattg tctctttaag ttctagcaat      600
gtgaagcagg aactatgatt atattgacta cataaatgaa gaaattgagg ctcagataca      660
ttaagtaatt ctcccagggt cacacagcta gaactggcaa agcctgggat tgatccatga      720
tcttccagca ttgaagaatc ataaatgtaa ataactgcaa ggccttttcc tcagaagagc      780
tcctggtgct tgcaccaacc cactagcact tgttctctac aggggaacat ctgtgggcct      840
gggaatcact gcacgtcgca agagatgttg cttctgatga attattgttc ctgtcagtgg      900
tgtgaaggca aaaaaaaaaa aaaa                                             924

<210> SEQ ID NO 63
<211> LENGTH: 1079
<212> TYPE: DNA
<213> ORGANISM: Homo sapien
```

<400> SEQUENCE: 63

```
agtcccaaga actcaataat ctcttatgtt ttcttttgaa gacttatttt aaatattaac      60
tatttcggtg cctgaatgga aaatatataaa cattagctca gagacaatgg ggtacctgtt    120
tggaatccag ctggcagcta taagcaccgt tgaaaactct gacaggcttt gtgccctttt    180
tattaaatgg cctcacatcc tgaatgcagg aatgtgttcg tttaaataaa cattaatctt    240
taatgttgaa ttctgaaaac acaaccataa atcatagttg gttttctgt gacaatgatc      300
tagtacatta tttcctccac agcaaaccta cctttccaga aggtggaaat tgtatttgca    360
acaatcaggg caaaacccac acttgaaaag cattttacaa tattatatct aagttgcaca    420
gaagacccca gtgatcacta ggaaatctac cacagtccag ttttctaat ccaagaaggt      480
caaacttcgg ggaataatgt gtccctcttc tgctgctgct ctgaaaaata ttcgatcaaa    540
acgaagttta caagcagcag ttattccaag attagagttc atttgtgtat cccatgtata    600
ctggcaatgt ttaggtttgc ccaaaaactc ccagacatcc acaatgttgt tgggtaaacc    660
accacatctg gtaacctctc gatcccttag atttgtatct cctgcaaata taactgtagc    720
tgactctgga gcctcttgca ttttctttaa aaccattttt aactgattca ttcgttccgc    780
agcatgccct ctggtgctct ccaaatggga tgtcataagg caaagctcat ttcctgacac    840
attcacatgc acacataaaa ggtttctcat cattttggta cttggaaaag gaataatctc    900
ttggcttttt aatttcactc ttgatttctt caacattata gctgtgaaat atccttcttc    960
atgacctgta ataatctcat aattacttga tctcttcttt aggtagctat aatatggggg   1020
aataacttcc tgtagaaata tcacatctgg gctgtacaaa gctaagtagg aacacaccc    1079
```

<210> SEQ ID NO 64
<211> LENGTH: 1001
<212> TYPE: DNA
<213> ORGANISM: Homo sapien

<400> SEQUENCE: 64

```
gaatgtgcaa cgatcaagtc agggtatctg tggtatccac cactttgagc atttatcgat      60
tctatatgtc aggaacattt caagttatct gttctagcaa ggaaatataa aatacttata    120
gttaactatg gcctatctac agtgcaacta aaaactagat tttattcctt tccacctgtg    180
ggtttgtatt catttaccac cctcttttca ttcccttcct cacccacaca ctgtgccggg    240
cctcaggcat atactattct actgtctgtc tctgtaagga ttatcatttt agcttccaca    300
tatgagagaa tgcatgcaaa gttttctctt ccatgtctgg cttatttcac ttaacataat    360
gacctccgct tccatccatg ttatttatat tacccaatag tgttcataaa tatatataca    420
cacatatata ccacattgca tttgtccaat tattcattga cggaaactgg ttaatgttat    480
atcgttgcta ttgtggatag tgctgcaata aacacgcaag tggggatata atttgaagag    540
ttttttttgtt gatgttcctc caaatttaa gattgttttg tctatgtttg tgaaaatggc      600
gttagtattt tcatagagat tgcattgaat ctgtagattg ctttgggtaa gtatggttat    660
tttgatggta ttaattttt cattccatga agatgagatg tctttccatt gtttgtgtcc     720
tctacatttt ctttcatcaa agttttgttg tattttgaa gtagatgtat ttcaccttat    780
agatcaagtg tattccctaa atatttatt tttgtagcta ttgtagatga aattgccttc     840
ttgatttctt tttcacttaa ttcattatta gtgtatggaa atgttatgga tttttatttg    900
ttggttttta atcaaaaact gtattaaact tagagttttt tgtggagttt ttaagttttt   960
```

```
ctagatataa gatcatgaca tctaccaaaa aaaaaaaaaa a                    1001
```

<210> SEQ ID NO 65
<211> LENGTH: 575
<212> TYPE: DNA
<213> ORGANISM: Homo sapien

<400> SEQUENCE: 65

```
acttgatata aaaaggatat ccataatgaa tattttatac tgcatccttt acattagcca    60
ctaaatacgt tattgcttga tgaagacctt tcacagaatc ctatggattg cagcatttca   120
cttggctact tcatacccat gccttaaaga ggggcagttt ctcaaaagca gaaacatgcc   180
gccagttctc aagttttcct cctaactcca tttgaatgta agggcagctg ccccccaatg   240
tggggaggtc cgaacatttt ctgaattccc attttcttgt tcgcggctaa atgacagttt   300
ctgtcattac ttagattccc gatctttccc aaggtgttg atttacaaag aggccagcta   360
atagccagaa atcatgaccc tgaaagagag atgaaatttc aagctgtgag ccaggcagga   420
gctccagtat ggcaaaggtt cttgagaatc agccatttgg tacaaaaaag attttaaag   480
cttttatgtt ataccatgga gccatagaaa ggctatggat tgtttaagaa ctattttaaa   540
gtgttccaga cccaaaaagg aaaaaaaaaa aaaaa                              575
```

<210> SEQ ID NO 66
<211> LENGTH: 831
<212> TYPE: DNA
<213> ORGANISM: Homo sapien

<400> SEQUENCE: 66

```
attgggctcc ttctgctaaa cagccacatt gaaatggttt aaaagcaagt cagatcaggt    60
gatttgtaaa attgtattta tctgtacatg tatgggcttt taattcccac caagaaagag   120
agaaattatc ttttttagtta aaaccaaatt tcacttttca aaatatcttc caacttattt   180
attggttgtc actcaattgc ctatatatat atatatatat gtgtgtgtgt gtgtgtgcgc   240
gtgagcgcac gtgtgtgtat gcgtgcgcat gtgtgtgtat gtgtattatc agacataggt   300
ttctaacttt tagatagaag aggagcaaca tctatgccaa atactgtgca ttctacaatg   360
gtgctaatct cagacctaaa tgatactcca tttaatttaa aaaagagttt taaataatta   420
tctatgtgcc tgtatttccc ttttgagtgc tgcacaacat gttaacatat tagtgtaaaa   480
gcagatgaaa caaccacgtg ttctaaagtc tagggattgt gctataatcc ctatttagtt   540
caaaattaac cagaattctt ccatgtgaaa tggaccaaac tcatattatt gttatgtaaa   600
tacagagttt taatgcagta tgacatccca caggggaaaa gaatgtctgt agtgggtgac   660
tgttatcaaa tattttatag aatacaatga acggtgaaca gactggtaac ttgtttgagt   720
tcccatgaca gatttgagac ttgtcaatag caaatcattt ttgtatttaa attttttgtac   780
tgatttgaaa aacatcatta aatatcttta aaagtaaaaa aaaaaaaaaa a             831
```

<210> SEQ ID NO 67
<211> LENGTH: 590
<212> TYPE: DNA
<213> ORGANISM: Homo sapien

<400> SEQUENCE: 67

```
gtgctctgtg tatttttta ctgcattaga cattgaatag taatttgcgt taagatacgc    60
ttaaaggctc tttgtgacca tgtttccctt tgtagcaata aaatgttttt tacgaaaact   120
ttctccctgg attagcagtt taaatgaaac agagttcatc aatgaaatga gtatttaaaa   180
```

```
taaaaatttg ccttaatgta tcagttcagc tcacaagtat tttaagatga ttgagaagac      240
ttgaattaaa gaaaaaaaaa ttctcaatca tattttttaaa atataagact aaaattgttt      300
ttaaaacaca tttcaaatag aagtgagttt gaactgacct tatttatact cttttttaagt     360 ttgttccttt tccctgtgcc tgtgtcaaat cttcaagtct tgctgaaaat acatttgata      420
caaagttttc tgtagttgtg ttagttcttt tgtcatgtct gttttttggct gaagaaccaa     480 gaagcagact tttcttttaa aagaattatt tctctttcaa atatttctat cctttttaaa      540
aaattccttt ttatggctta tatacctaca tatttaaaaa aaaaaaaaaa                  590

<210> SEQ ID NO 68
<211> LENGTH: 291
<212> TYPE: DNA
<213> ORGANISM: Homo sapien
<220> FEATURE:
<221> NAME/KEY: misc_feature
<222> LOCATION: (1)...(291)
<223> OTHER INFORMATION: n = A,T,C or G

<400> SEQUENCE: 68 gttcccttttt ccggtcggcg tggtcttgcg agtggagtgt ccgctgtgcc cgggcctgca     60
ccatgagcgt cccggccttc atcgacatca gtgaagaaga tcaggctgct gagcttcgtg     120
cttatctgaa atctaaagga gctgagattt cagaagagaa ctcggaaggt ggacttcatg     180
ttgatttagc tcaaattatt gaagcctgtg atgtgtgtct gaaggaggat gataaagatg     240
ttgaaagtgt gatgaacagt ggggnatcct actcttgatc cggaanccna c              291

<210> SEQ ID NO 69
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 69
tctatgagca tgccaaggct ctgtgggagg atgaaggagt gcgtgcctgc tacgaacgct      60
ccaacgagta ccagctgatt gactgtgccc agtacttcct ggacaagatc gacgtgatca     120
agcaggctga ctatgtgccg agcgatcagg acctgcttcg ctgccgtgtc ctgacttctg     180
gaatctttga gaccaagttc caggtggacn aagtcaactt ccacatgntt gacgtgggtg     240
gccagcgcga tgaacgccgc aagtggatcc agtgcttcaa cgatgtgact gccatcatct     300
t                                                                     301

<210> SEQ ID NO 70
<211> LENGTH: 201
<212> TYPE: DNA
<213> ORGANISM: Homo sapien

<400> SEQUENCE: 70
gcggctcttc ctcgggcagc ggaagcggcg cggcggtcgg agaagtggcc taaaacttcg      60
gcgttgggtg aaagaaaatg gcccgaacca agcagactgc tcgtaagtcc accgtggga      120 aagcccccccg caaacagctg gccacgaaag ccgccaggaa aagcgctccc tctaccggcg     180
gggtgaagaa gcctcatcgc t                                               201

<210> SEQ ID NO 71
```

```
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 71
gccggggtag tcgccgncgc cgccgccgct gcagccactg caggcaccgc tgccgccgcc      60
tgagtagtgg gcttaggaag gaagaggtca tctcgctcgg agcttcgctc ggaagggtct     120
ttgttccctg cagccctccc acgggaatga caatggataa aagtgagctg gtacanaaag     180
ccaaactcgc tgagcaggct gagcgatatg atgatatggc tgcagccatg aaggcagtca     240
cagaacaggg gcatgaactc ttcaacgaag agagaaatct gctctctggt gcctacaaga     300
a                                                                     301

<210> SEQ ID NO 72
<211> LENGTH: 251
<212> TYPE: DNA
<213> ORGANISM: Homo sapien
<220> FEATURE:
<221> NAME/KEY: misc_feature
<222> LOCATION: (1)...(251)
<223> OTHER INFORMATION: n = A,T,C or G

<400> SEQUENCE: 72 cttgggggt gttggggag agactgtggg cctggaaata aaacttgtct cctctaccac       60
caccctgtac cctagcctgc acctgtccac atctctgcaa agttcagctt ccttccccag    120
gtctctgtgc actctgtctt ggatgctctg gggagctcat gggtggagga gtctccacca    180
gagggaggct caggggactg gttgggccag ggatgaatat ttgagggata aaaattgtgt    240
aagagccaan g                                                         251

<210> SEQ ID NO 73
<211> LENGTH: 895
<212> TYPE: DNA
<213> ORGANISM: Homo sapien

<400> SEQUENCE: 73
tttttttttt tttttcccag gccctctttt tatttacagt gataccaaac catccacttg     60
caaattcttt ggtctcccat cagctggaat taagtaggta ctgtgtatct ttgagatcat    120
gtatttgtct ccactttggt ggatacaaga aaggaaggca cgaacagctg aaaaagaagg    180
gtatcacacc gctccagctg gaatccagca ggaacctctg agcatgccac agctgaacac    240
ttaaaagagg aaagaaggac agctgctctt catttatttt gaaagcaaat tcatttgaaa    300
gtgcataaat ggtcatcata agtcaaacgt atcaattaga ccttcaacct aggaaacaaa    360
attttttttt tctatttaat aatacaccac actgaaatta tttgccaatg aatcccaaag    420
atttggtaca aatagtacaa ttcgtatttg ctttcctctt tcctttcttc agacaaacac    480
caaataaaat gcaggtgaaa gagatgaacc acgactagag gctgacttag aaatttatgc    540
tgactcgatc taaaaaaaat tatgttggtt aatgttaatc tatctaaaat agagcatttt    600
gggaatgctt tcaaagaag gtcaagtaac agtcatacag ctagaaaagt ccctgaaaaa    660
aagaattgtt aagaagtata ataaccttt caaaacccac aatgcagctt agttttcctt     720
tatttatttg tggtcatgaa gactatcccc atttctccat aaaatcctcc ctccatactg    780
ctgcattatg gcacaaaaga ctctaagtgc caccagacag aaggaccaga gtttctgatt    840
```

```
ataaacaatg atgctgggta atgtttaaat gagaacattg gatatggatg gtcag        895
```

```
<210> SEQ ID NO 74
<211> LENGTH: 351
<212> TYPE: DNA
<213> ORGANISM: Homo sapien
<220> FEATURE:
<221> NAME/KEY: misc_feature
<222> LOCATION: (1)...(351)
<223> OTHER INFORMATION: n = A,T,C or G

<400> SEQUENCE: 74
tgtgcncagg ggatgggtgg gcngtggaga ngatgacaga aaggctggaa ggaangggggg    60
tgggtttgaa ggccanggcc aagggcct caggtccgnt tctgnnaagg gacagccttg     120
aggaaggagn catggcaagc catagctagg ccaccaatca gattaagaaa nnctgagaaa   180
nctagctgac catcactgtt ggtgnccagt ttcccaacac aatggaatnc caccacactg   240
gactagngga nccactagtt ctagagcggc cgccaccgcg gtggaacccc aacttttgcc   300
cctttagnga gggttaattg cgcgcttggc ntaatcatgg tcataagctg t            351
```

```
<210> SEQ ID NO 75
<211> LENGTH: 251
<212> TYPE: DNA
<213> ORGANISM: Homo sapien

<400> SEQUENCE: 75
tacttgacct tctttgaaaa gcattcccaa aatgctctat tttagataga ttaacattaa    60
ccaacataat ttttttaga tcgagtcagc ataaatttct aagtcagcct ctagtcgtgg    120
ttcatctctt tcacctgcat tttatttggt gtttgtctga agaaaggaaa gaggaaagca   180
aatacgaatt gtactatttg taccaaatct ttgggattca ttggcaaata atttcagtgt   240
ggtgtattat t                                                        251
```

```
<210> SEQ ID NO 76
<211> LENGTH: 251
<212> TYPE: DNA
<213> ORGANISM: Homo sapien

<400> SEQUENCE: 76
tatttaataa tacaccacac tgaaattatt tgccaatgaa tcccaaagat ttggtacaaa    60
tagtacaatt cgtatttgct ttcctctttc ctttcttcag acaaacacca aataaaatgc   120
aggtgaaaga gatgaaccac gactagaggc tgacttagaa atttatgctg actcgatcta   180
aaaaaaatta tgttggttaa tgttaatcta tctaaaatag agcattttgg gaatgctttt   240
caaagaaggt c                                                        251
```

```
<210> SEQ ID NO 77
<211> LENGTH: 351
<212> TYPE: DNA
<213> ORGANISM: Homo sapien
<220> FEATURE:
<221> NAME/KEY: misc_feature
<222> LOCATION: (1)...(351)
<223> OTHER INFORMATION: n = A,T,C or G

<400> SEQUENCE: 77
actcaccgtg ctgtgtgctg tgtgcctgct gcctggcagc ctggccctgc cgctgctcag    60
gaggcgggag gcatgagtga gctacagtgg gaacaggctc aggactatct caagagannn   120
```

-continued

| | |
|---|---|
| tatctctatg actcagaaac aaaaaatgcc aacagtttag aagccaaact caaggagatg | 180 |
| caaaaattct ttggcctacc tataactgga atgttaaact cccgcgtcat agaaataatg | 240 |
| cagaagccca gatgtggagt gccagatgtt gcagaatact cactatttcc aaatagccca | 300 |
| aaatggactt ccaaagtggt cacctacagg atcgtatcat atactcgaga c | 351 |

<210> SEQ ID NO 78
<211> LENGTH: 1574
<212> TYPE: DNA
<213> ORGANISM: Homo sapien

<400> SEQUENCE: 78

| | |
|---|---|
| gccctggggg cggaggggag gggcccacca cggccttatt tccgcgagcg ccggcactgc | 60 |
| ccgctccgag cccgtgtctg tcgggtgccg agccaacttt cctgcgtcca tgcagccccg | 120 |
| ccggcaacgg ctgcccgctc cctggtccgg gcccaggggc ccgcgcccca ccgcccgct | 180 |
| gctcgcgctg ctgctgttgc tcgccccggt ggcggcgccc gcggggtccg gggaccccga | 240 |
| cgaccctggg cagcctcagg atgctggggt cccgcgcagg ctcctgcagc aggcggcgcg | 300 |
| cgcggcgctt cacttcttca acttccggtc cggctcgccc agcgcgctgc gagtgctggc | 360 |
| cgaggtgcag gagggccgcg cgtggattaa tccaaaagag ggatgtaaag ttcacgtggt | 420 |
| cttcagcaca gagcgctaca acccagagtc tttacttcag gaaggtgagg acgtttggg | 480 |
| gaaatgttct gctcgagtgt ttttcaagaa tcagaaaccc agaccaacta tcaatgtaac | 540 |
| ttgtacacgg ctcatcgaga aaagaaaag acaacaagag gattacctgc tttacaagca | 600 |
| aatgaagcaa ctgaaaaacc ccttggaaat agtcagcata cctgataatc atggacatat | 660 |
| tgatccctct ctgagactca tctgggattt ggctttcctt ggaagctctt acgtgatgtg | 720 |
| ggaaatgaca acacaggtgt cacactacta cttggcacag ctcactagtg tgaggcagtg | 780 |
| gaaaactaat gatgatacaa ttgattttga ttatactgtt ctacttcatg aattatcaac | 840 |
| acaggaaata attccctgtc gcattcactt ggtctggtac cctggcaaac ctcttaaagt | 900 |
| gaagtaccac tgtcaagagc tacagacacc agaagaagcc tccggaactg aagaaggatc | 960 |
| agctgtagta ccaacagagc ttagtaattt ctaaaaagaa aaatgatct tttcccgact | 1020 |
| tctaaacaag tgactatact agcataaatc attcttctag taaacagct aaggtataga | 1080 |
| cattctaata atttgggaaa acctatgatt acaagtaaaa actcagaaat gcaaagatgt | 1140 |
| tggttttttg tttctcagtc tgctttagct tttaactctg gaagcgcatg cacactgaac | 1200 |
| tctgctcagt gctaaacagt caccagcagg ttcctcaggg tttcagccct aaaatgtaaa | 1260 |
| acctggataa tcagtgtatg ttgcaccaga atcagcattt tttttttaac tgcaaaaaat | 1320 |
| gatggtctca tctctgaatt tatatttctc attcttttga acatactata gctaatatat | 1380 |
| tttatgttgc taaattgctt ctatctagca tgttaaacaa agataatata ctttcgatga | 1440 |
| aagtaaatta taggaaaaaa attaactgtt ttaaaagaa cttgattatg ttttatgatt | 1500 |
| tcaggcaagt attcattttt aacttgctac ctacttttaa ataaatgttt acatttctaa | 1560 |
| aaaaaaaaaa aaaa | 1574 |

<210> SEQ ID NO 79
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 79

| | | |
|---|---|---|
| catactgtga attgttcttg actccttttc ttgacattca gttttcanaa tttccatctt | 60 |
| tcttctggaa ctaatgtgct gttctcttga ctgcctgctg ggccagcatc cgattgccag | 120 |
| ccagaaacgt cacactgccc aagatggcca ggtacttcaa ggtctggaac atgttgagct | 180 |
| gagtccagta gacatacatg agtcccagca tagcagcatg tcccaggtga aatataatcg | 240 |
| tgctaggagc aaaagtgaag ttggagacat tggcaccaat ccggatccac tagttctaga | 300 |
| gcggccgcca ccgcggtgga gctccagctt ttgttcccct tagtgagggt taattgcgcg | 360 |
| cttggcgtaa tcatggncat agctgtttcc tgtgtgaaat t | 401 |

<210> SEQ ID NO 80
<211> LENGTH: 301
<212> TYPE: DNA
<213> ORGANISM: Homo sapien

<400> SEQUENCE: 80

| | | |
|---|---|---|
| aaaaatgaaa catctatttt agcagcaaga ggctgtgagg gatggggtag aaaaggcatc | 60 |
| ctgagagagt tctagaccga cccaggtcct gtggcacact atacgggtca ggaggggtgg | 120 |
| aagacaggcc taagctctag gacggtgaat ctcggggcta tttgtggatt tgttagaaac | 180 |
| agacattctt ttggcctttt cctggcactg gtgttgccgg caggtgggca gaagtgagcc | 240 |
| accagtcact gttcagtcat tgccaccaca gatcttcagc agaatcttcc ggtaatcccc | 300 |
| t | 301 |

<210> SEQ ID NO 81
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 81

| | | |
|---|---|---|
| tagccaggtt gctcaagcta attttattct ttcccaacag gatccatttg gaaaatatca | 60 |
| agcctttaga atgtggcagc aagagaaagc ggactacgca ggaacgggga gtttgggaga | 120 |
| agctctcctg gtgttgactt agggatgaag gctccaggct gctgccagaa atggagtcac | 180 |
| cagcagaaga actgntttct ctgataagga tgtcccacca ttttcaagct gttcgttaaa | 240 |
| gttacacagg tccttcttgc agcagtaagt accgttagct cattttccct caagcgggtt | 300 |
| t | 301 |

<210> SEQ ID NO 82
<211> LENGTH: 201
<212> TYPE: DNA
<213> ORGANISM: Homo sapien
<220> FEATURE:
<221> NAME/KEY: misc_feature
<222> LOCATION: (1)...(201)
<223> OTHER INFORMATION: n = A,T,C or G

<400> SEQUENCE: 82

| | | |
|---|---|---|
| tcaacagaca aaaaagttt attgaataca aaactcaaag gcatcaacag tcctgggccc | 60 |
| aagagatcca tggcaggaag tcaagagttc tgcttcaggg tcggtctggg cagccctgga | 120 |
| agaagtcatt gcacatgaca gtgatgagtg ccaggaaaac agcatactcc tggaaagtcc | 180 | acctgctggn cactgnttca t                                              201

<210> SEQ ID NO 83
<211> LENGTH: 251
<212> TYPE: DNA
<213> ORGANISM: Homo sapien
<220> FEATURE:
<221> NAME/KEY: misc_feature
<222> LOCATION: (1)...(251)
<223> OTHER INFORMATION: n = A,T,C or G

<400> SEQUENCE: 83
gtaaggagca tactgtgccc atttattata gaatgcagtt aaaaaaaata ttttgaggtt      60
agcctctcca gtttaaaagc acttaacaag aaacacttgg acagcgatgc aatggtctct    120
cccaaaccgg ctccctctta ccaagtaccg taaacagggt ttgagaacgt tcaatcaatt    180
tcttgatatg aacaatcaaa gcatttaatg caaacatatt tgcttctcaa anaataaaac    240
cattttccaa a                                                         251

<210> SEQ ID NO 84
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 84
agtttataat gttttactat gatttagggc ttttttttca aagaacaaaa attataagca      60
taaaaactca ggtatcagaa agactcaaaa ggctgttttt cactttgttc agattttgtt    120
tccaggcatt aagtgtgtca tacagttgtt gccactgctg ttttccaaat gtccgatgtg    180
tgctatgact gacaactact tttctctggg tctgatcaat tttgcagtan accattttag    240
ttcttacggc gtcnataaca aatgcttcaa catcatcagc tccaatctga agtcttgctg    300
c                                                                    301

<210> SEQ ID NO 85
<211> LENGTH: 201
<212> TYPE: DNA
<213> ORGANISM: Homo sapien

<400> SEQUENCE: 85
tatttgtgta tgtaacattt attgacatct acccactgca agtatagatg aataagacac      60
agtcacacca taaaggagtt tatccttaaa aggagtgaaa gacattcaaa aaccaactgc    120
aataaaaaag ggtgacataa ttgctaaatg gagtggagga acagtgctta tcaattcttg    180
attgggccac aatgatatac c                                              201

<210> SEQ ID NO 86
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 86
tttataaaat attttattta cagtagagct ttacaaaaat agtcttaaat taatacaaat      60
cccttttgca ataaactta tatgactatc ttctcaaaaa cgtgacattc gattataaca    120

```
cataaactac atttatagtt gttaagtcac cttgtagtat aaatatgttt tcatctttt      180 tttgtaataa ggtacatacc aataacaatg aacaatggac aacaaatctt attttgntat     240
tcttccaatg taaaattcat ctctggccaa aacaaaatta accaagaaaa agtaaaacaa     300
t                                                                    301

<210> SEQ ID NO 87
<211> LENGTH: 351
<212> TYPE: DNA
<213> ORGANISM: Homo sapien
<220> FEATURE:
<221> NAME/KEY: misc_feature
<222> LOCATION: (1)...(351)
<223> OTHER INFORMATION: n = A,T,C or G

<400> SEQUENCE: 87
aaaaaagatt taagatcata ataggtcat tgttgtcaca acacatttca gaatcttaaa      60
aaaacaaaca ttttggcttt ctaagaaaaa gacttttaaa aaaatcaat tccctcatca     120 ctgaaaggac ttgtacattt ttaaacttcc agtctcctaa ggcacagtat ttaatcagaa    180
tgccaatatt accaccctgc tgtagcanga ataaagaagc aagggattaa cacttaaaaa    240
aacngccaaa ttcctgaacc aaatcattgg cattttaaaa aagggataaa aaaacnggnt    300 aagggggggga gcattttaag taaagaaggg ccaagggtgg tatgccngga c             351

<210> SEQ ID NO 88
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 88
gttttaggtc tttaccaatt tgattggttt atcaacaggg catgaggttt aaatatatct      60
ttgaggaaag gtaaagtcaa atttgacttc ataggtcatc ggcgtcctca ctcctgtgca    120
ttttctggtg gaagcacaca gttaattaac tcaagtgtgg cgntagcgat gcttttcat    180 ggngtcattt atccacttgg tgaacttgca cacttgaatg naaactcctg ggtcattggg    240
ntggccgcaa gggaaaggtc cccaagacac caaaccttgc agggtaccta tgcacaccaa    300
c                                                                    301

<210> SEQ ID NO 89
<211> LENGTH: 591
<212> TYPE: DNA
<213> ORGANISM: Homo sapien

<400> SEQUENCE: 89
tttttttttt tttttttatt aatcaaatga ttcaaaacaa ccatcattct gtcaatgccc      60
aagcacccag ctggtcctct ccccacatgt cacactctcc tcagcctctc ccccaaccct    120
gctctccctc ctcccctgcc ctagcccagg acagagtct aggaggagcc tggggcagag     180
ctggaggcag gaagagagca ctggacagac agctatggtt tggattgggg aagagattag    240
gaagtaggtt cttaaagacc ctttttttagt accagatatc cagccatatt cccagctcca    300
ttattcaaat catttcccat agcccagctc ctctctgttc tcccccctact accaattctt    360 tggctcttac acaattttta tccctcaaat attcatccct ggcccaacca gtcccctgag    420
```

-continued

| | | |
|---|---|---|
| cctccctctg gtggagactc ctccacccat gagctcccca gagcatccaa gacagagtgc | 480 | |
| acagagacct ggggaaggaa gctgaacttt gcagagatgt ggacaggtgc aggctagggt | 540 | |
| acagggtggt ggtagaggag acaagtttta tttccaggcc cacagtctct c | 591 | |

<210> SEQ ID NO 90
<211> LENGTH: 1978
<212> TYPE: DNA
<213> ORGANISM: Homo sapien

<400> SEQUENCE: 90

| | | |
|---|---|---|
| tttttttttt tttttttatca aatgaatact ttattagaga cataacacgt ataaaataaa | 60 | |
| tttcttttca tcatggagtt accagatttt aaaaccaacc aacactttct catttttaca | 120 | |
| gctaagacat gttaaattct taaatgccat aatttttgtt caactgcttt gtcattcaac | 180 | |
| tcacaagtct agaatgtgat taagctacaa atctaagtat tcacagatgt gtcttaggct | 240 | |
| tggtttgtaa caatctagaa gcaatctgtt tacaaaagtg ccaccaaagc attttaaaga | 300 | |
| aaccaattta atgccaccaa acataagcct gctatacctg ggaaacaaaa aatctcacac | 360 | |
| ctaaattcta gcagagtaaa cgattccaac tagaatgtac tgtatatcca tatggcacat | 420 | |
| ttatgacttt gtaatatgta attcataata caggtttagg tgtgtggtat ggagctagga | 480 | |
| aaaccaaagt agtaggatat tatagaaaag atctgatgtt aagtataaag tcatatgcct | 540 | |
| gatttcctca aacctttgt ttttcctcat gtcttctgtc tttatatttt tatcacaaac | 600 | |
| caagatctaa caggggttctt tctagaggat tattagataa gtaacacttg atcattaagc | 660 | |
| acggatcatg ccactcattc atggttgttc tatgttccat gaactctaat agcccaactt | 720 | |
| atacatggca ctccaagggg atgcttcagc cagaaagtaa agggctgaaa aagtagaaca | 780 | |
| atacaaaagc cctcgtgtgg tgggaactgt ggcctcactc ttacttgtcc ttccattcaa | 840 | |
| aacagtttgg cacctttcca tgacgaggat ctctacaggt aggttaaaat acttttctgt | 900 | |
| gctattcagc cagaaatagt ttttgtgctg gatatgattt taaaacagat tttgtctgtc | 960 | |
| accagtgcaa aaacattaca gatgtctggg ctaatacaaa aacacataag aatctacaac | 1020 | |
| tttatattta atactctatt caaatttaac tcaaagtaat gcaaaataat tagaagtaaa | 1080 | |
| aacttaattc ttctgagagc tctatttgga aaagcttcac atatccacac acaaatatgg | 1140 | |
| gtatattcat gcacagggca aacaactgta ttctgaagca taaataaact caaagtaaga | 1200 | |
| catcagtagc tagataccag ttccagtatt ggttaatggt ctctggggat cccattttaa | 1260 | |
| gcactctcag atgaggatct tgctcagttg ttagactatc attagtttga ttaagcaact | 1320 | |
| gaagtttact tcataaatta cttttttccta tatccaggac tctgcctgag aaattttata | 1380 | |
| cattcctcca aagtaagta ttctccaaag gtaagtattt gactattaac acaaaggcaa | 1440 | |
| tgtgattatt gcataatgac actaaatatt atgtggcttt tctgttaggt ttataagttt | 1500 | |
| tcaatgatca gttcaagaaa atgcagatca tatataacta aggttttaca ccagtggttg | 1560 | |
| acaaactatg gccacaggc taaacccagc ctccccttgt ttttataaat aagtttatt | 1620 | |
| agacataacc acactcattc atttctgtat tgtgtatagc tgctttcacg ctatactagc | 1680 | |
| agaactgaat agttgtgaca gagactgtat ggaccgtgaa gcataaatat ttaccatctg | 1740 | |
| gcccattcta aaaaagtgt gccaattcct ggtttacact aaaatataga gtttagtggg | 1800 | |
| aagcctattt gaaatgtgtt ttttttaggg gctgtaatta ccaattaaaa ttaaggttca | 1860 | |
| ggtgactcag caaccaaaca aaagggatac taattttta tgaacaatat atttgtattt | 1920 | |
| tatggacata aaaggaaact ttcagaaaga aaggaggaa aataaagggg gaaaggga | 1978 | |

<210> SEQ ID NO 91
<211> LENGTH: 895
<212> TYPE: DNA
<213> ORGANISM: Homo sapien

<400> SEQUENCE: 91

| | | | | | |
|---|---|---|---|---|---|
| tttttttttt | tttttcttg | tttaaaaaaa | ttgttttcat | tttaatgatc | tgagttagta | 60 |
| acaaacaaat | gtacaaaatt | gtctttcaca | tttccataca | ttgtgttatg | gaccaaatga | 120 |
| aaacgctgga | ctacaaatgc | aggtttcttt | atatccttaa | cttcaattat | tgtcacttat | 180 |
| aaataaaggt | gatttgctaa | cacatgcatt | tgtgaacaca | gatgccaaaa | attatacatg | 240 |
| taagttaatg | cacaaccaag | agtatacact | gttcatttgt | gcagttatgc | gtcaaatgcg | 300 |
| actgacacag | aagcagttat | cctgggatat | ttcactctat | atgaaaagca | tcttggagaa | 360 |
| atagattgaa | atacagtttta | aaacaaaaat | tgtattctac | aaatacaata | aaatttgcaa | 420 |
| cttgcacatc | tgaagcaaca | tttgagaaag | ctgcttcaat | aaccctgctg | ttatattggt | 480 |
| tttataggta | tatctccaaa | gtcatgggtt | gggatatagc | tgctttaaag | aaaataaata | 540 |
| tgtatattaa | aaggaaaatc | acactttaaa | aatgtgagga | aagctttgaa | acagtcttaa | 600 |
| atgcatgagt | ccatctacat | attttcaagt | tttggaaaca | gaaagaagtt | tagaattttc | 660 |
| aaagtaatct | gaaaactttc | taagccattt | taaaataaga | ttttttttccc | catctttcca | 720 |
| atgtttccta | tttgatagtg | taatacagaa | atgggcagtt | tctagtgtca | acttaactgt | 780 |
| gctaattcat | aagtcattat | acatttatga | cttaagagtt | caaataagtg | gaaattgggt | 840 |
| tataatgaaa | atgacaaggg | ggcccttca | gcagccactc | atctgaacta | gtaat | 895 |

<210> SEQ ID NO 92
<211> LENGTH: 1692
<212> TYPE: DNA
<213> ORGANISM: Homo sapien

<400> SEQUENCE: 92

| | | | | | |
|---|---|---|---|---|---|
| tttttttttt | ttttttaactt | ttagcagtgt | ttattttttgt | taaagaaac | caattgaatt | 60 |
| gaaggtcaag | acaccttctg | attgcacaga | ttaaacaaga | aagtattact | tatttcaact | 120 |
| ttacaaagca | tcttattgat | ttaaaaagat | ccatactatt | gataaagttc | accatgaaca | 180 |
| tatatgtaat | aaggagacta | aaatattcat | tttacatatc | tacaacatgt | atttcatatt | 240 |
| tctaatcaac | cacaaatcat | ataggaaaat | atttaggtcc | atgaaaaagt | ttcaaaacat | 300 |
| taaaaaatta | aagttttgaa | acaaatcaca | tgtgaaagct | cattaaataa | taacattgac | 360 |
| aaaataaatag | ttaatcagct | ttacttatta | gctgctgcca | tgcatttctg | gcattccatt | 420 |
| ccaagcgagg | gtcagcatgc | agggtataat | ttcatactat | gcgaccgtaa | agagctacag | 480 |
| ggcttatttt | tgaagtgaaa | tgtcacaggg | tctttcattc | tctttcaaag | gaagatcact | 540 |
| catggctgct | aaactgttcc | catgaagagt | accaaaaaag | cacctttctg | aaatgttact | 600 |
| gtgaagattc | atgacaacat | attttttttta | acctgttttg | aaggagtttt | gtttaggaga | 660 |
| ggggatgggc | cagtagatgg | agggtatctg | agaagcccctt | ttctgtttta | aaatataatg | 720 |
| attcactgat | gtttatagta | tcaacagtct | tttaagaaca | atgaggaatt | aaaactacag | 780 |
| gatacgtgga | atttaaatgc | aaattgcatt | catggatata | cctacatctt | gaaaaacttg | 840 |
| aaaaggaaaa | actattccca | aagaaggtcc | tgatacttaa | gacagcttgc | tgggtttgat | 900 |
| caaagcagaa | agcatatact | ttcaagtgag | aaaacagcag | tggcaggctt | gagtcttcca | 960 |

| | |
|---|---|
| agcaatcaaa tctgtaaagc agatggttac tagtaagtct agttatggga gtctgagttc | 1020 |
| taactcatgc tgtgcttgct ggatttgctg gctcttttcc gctctctgtg atgctggact | 1080 |
| ggcttgtcag gtgacatgct ctcaaagttg tgactggact cgttgtgctg ccgggtgtac | 1140 |
| ctcttgcact tgcaggcagt gactactgtg attttgtagg tgcgtgtgct gccatcttgg | 1200 |
| cactgcagct ggattctctg gtacgggtt ttgtcattga cacaccgcca ctcctgggag | 1260 |
| ctcctcctgc tccagtactt tgttccatag cctcctccaa tccagttagg gagcactggc | 1320 |
| aggggcaagc actcgccagc acacaccagc tccttcagag gctgatgct ggtgcactgg | 1380 |
| ccatcagaga tgtatttggt ggaacgcagt tcccggcaac ccacttgaac ccgagtgttc | 1440 |
| cgatccagtc cagtgttact gaaatgcctg cctccatttc tggcttgatt caacgtgctg | 1500 |
| ttgctgctgg ggtgtgctgg aacaggttta accacatgtg aataaaggat ttctgtggca | 1560 |
| tcatttttaa aagccaaaca gcttttcatt aggatgcatg caaggggaag agatagaaa | 1620 |
| tgaatggcag gaggaagcat ggtgagtaga ggatttgctt gactgaagag ctggttaatt | 1680 |
| cttttgcctc tg | 1692 |

<210> SEQ ID NO 93
<211> LENGTH: 251
<212> TYPE: DNA
<213> ORGANISM: Homo sapien

<400> SEQUENCE: 93

| | |
|---|---|
| cccaccctac ccaaatatta gacaccaaca cagaaaagct agcaatggat tcccttctac | 60 |
| tttgttaaat aaataagtta aatatttaaa tgcctgtgtc tctgtgatgg caacagaagg | 120 |
| accaacaggc cacatcctga taaaggtaa gagggggtg gatcagcaaa agacagtgc | 180 |
| tgtgggctga ggggacctgg ttcttgtgtg ttgcccctca agactcttcc cctacaaata | 240 |
| actttcatat g | 251 |

<210> SEQ ID NO 94
<211> LENGTH: 735
<212> TYPE: DNA
<213> ORGANISM: Homo sapien

<400> SEQUENCE: 94

| | |
|---|---|
| tttttttttt ttttttccact ctcagttta tttctgggac taaatttggg tcagagctgc | 60 |
| agagaaggga tgggccctga gcttgaggat gaaagtgccc cagggagatt gagacgcaac | 120 |
| ccccgccctg gacagttttg gaaattgttc ccagggttca actagagaga cacggtcagc | 180 |
| ccaatgtggg ggaagcagac cctgagtcca ggagacatgg ggtcagggc tggagagatg | 240 |
| aacattctca acatctctgg gaaggaatga gggtctgaaa ggagtgtcag ggctgtccct | 300 |
| gcagcaggtg gggatgccgg tgtgctgagt cctgggatga ctcaggagtt ggcctggatg | 360 |
| gtttcctgga tccacttggt gaacttgcag aggttcgtgt agacacccgg tctgttgggc | 420 |
| cgggcacaag gtaatctcc ccaggacacg agtccctgca gggagccatt gcagaccaca | 480 |
| ggcccccag aatcaccctg gcaggagtct ctacctgctt tgtcaccggc gcagaacatg | 540 |
| gtgtcatcta tctgtctcgg gtaagcatcc tcgcaccttt tctgacttag cacgctgata | 600 |
| ttcaagcact ggaggacctt agggaagtgc acttggggc tcttggttgt cccccagcca | 660 |
| gacaccaagc actttgtccc agcagaggga caatgagagg agacgttgat gggtctgaca | 720 |
| tctttagtgg gacga | 735 |

```
<210> SEQ ID NO 95
<211> LENGTH: 578
<212> TYPE: DNA
<213> ORGANISM: Homo sapien

<400> SEQUENCE: 95
cttgccttct cttaggcttt gaagcatttt tgtctgtgct ccctgatctt caggtcacca      60
ccatgaagtt cttagcagtc ctggtactct tgggagtttc catctttctg gtctctgccc     120
agaatccgac aacagctgct ccagctgaca cgtatccagc tactggtcct gctgatgatg     180
aagcccctga tgctgaaacc actgctgctg caaccactgc gaccactgct gctcctacca     240
ctgcaaccac cgctgcttct accactgctc gtaaagacat tccagtttta cccaaatggg     300
ttggggatct cccgaatggt agagtgtgtc cctgagatgg aatcagcttg agtcttctgc     360
aattggtcac aactattcat gcttcctgtg atttcatcca actacttacc ttgcctacga     420
tatcccettt atctctaatc agtttatttt ctttcaaata aaaataact atgagcaaca     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaa                             578

<210> SEQ ID NO 96
<211> LENGTH: 594
<212> TYPE: DNA
<213> ORGANISM: Homo sapien

<400> SEQUENCE: 96
atggcaaaga atggacttgt aatttgcatc ctggtgatca ccttactcct ggaccagacc      60
accagccaca catccagatt aaaagccagg aagcacagca acgtcgagt gagagacaag      120
gatggagatc tgaagactca aattgaaaag ctctggacag aagtcaatgc cttgaaggaa     180
attcaagccc tgcagacagt ctgtctccga ggcactaaag ttcacaagaa atgctacctt     240
gcttcagaag gtttgaagca tttccatgag gccaatgaag actgcatttc caaggagga      300
atcctggtta tccccaggaa ctccgacgaa atcaacgccc tccaagacta tggtaaaagg     360
agcctgccag gtgtcaatga cttttggctg gcatcaatg acatggtcac ggaaggcaag     420
tttgttgacg tcaacggaat cgctatctcc ttcctcaact gggaccgtgc acagcctaac     480
ggtggcaagc gagaaaactg tgtcctgttc tcccaatcag ctcagggcaa gtggagtgat     540
gaggcctgtc gcagcagcaa gagatacata tgcgagttca ccatccctca atag          594

<210> SEQ ID NO 97
<211> LENGTH: 3101
<212> TYPE: DNA
<213> ORGANISM: Homo sapien

<400> SEQUENCE: 97
tgttggggcc tcagcctccc aagtagctgg gactacaggt gcctgccacc acgcccagct      60
aattttttgt atattttta gtagagacgg ggtttcaccg tggtctcaat ctcctgacct     120
cgtgatctgc cagccttggc ctcccaaagt gtattctctt tttattatta ttattatttt     180
tgagatggag tctgtctctg tcgcccaggc tggagtgcag tggtgcgatc tctgctcact     240
gcaagctccg cctcctgggt tcatgccatt ctcctgcctc agcctcccga gtagctggga     300
ctacaggccc ctgccaccac acccggctaa ttttttgtat tttagtaga cagggttt     360
caccatgtta gccagggtgg tctctatctt ctgacctcgt gatccgcctg cctcagtctc     420
tcaaagtgct gggattacag gcgtgagcca ccgcgaccag ccaactattg ctgttattt     480
```

```
ttaaatatat tttaaagaaa caattagatt tgttttcttt ctcattcttt tacttctact    540
cttcatgtat gtataattat atttgtgttt tctattacct tttctccttt tactgtattg    600
gactataata attgtgctca ctaatttctg ttcactaata ttatcagctt agataatact    660 ttaatttta acttatatat tgagtattaa attgatcagt tttatttgta attatctatc    720
ttccgcttgg ctgaatataa cttcttaagc ttataacttc ttgttctttc catgttattt    780
ttttcttttt tttaatgtat tgaatttctt ctgacactca ttctagtaac tttttctcg    840 gtgtgcaacg taagtataa tttgtttctc agatttgaga tctgccataa gtttgaggct    900 ttatttttt tttttatttg ctttatggca agtcggacaa cctgcatgga tttggcatca    960
atgtagtcac ccatatctaa gagcagcact tgcttcttag catgatgagt tgtttctgga   1020
ttgtttcttt attttactta tattcctggt agattcttat attttccctt caactctatt   1080
cagcatttta ggaattctta ggactttctg agaattttag ctttctgtat taaatgtttt   1140
taatgagtat tgcattttct caaaaagcac aaatatcaat agtgtacaca tgaggaaaac   1200
tatatatata ttctgttgca gatgacagca tctcataaca aaatcctagt tacttcattt   1260
aaaagacagc tctcctccaa tatactatga ggtaacaaaa atttgtagtg tgtaattttt   1320
ttaatattag aaaactcatc ttacattgtg cacaaatttc tgaagtgata atacttcact   1380 gttttctat agaagtaact taatattggc aaaattactt atttgaattt aggttttggc   1440
tttcatcata tacttcctca ttaacatttc cctcaatcca taaatgcaat ctcagtttga   1500
atcttccatt taacccagaa gttaattttt aaaaccttaa taaaatttga atgtagctag   1560
atattatttg ttggttacat attagtcaat aatttatatt acttacaatg atcagaaaat   1620
atgatctgaa tttctgctgt cataaattca ataacgtatt ttaggcctaa acctttccat   1680
ttcaaatcct tgggtctggt aattgaaaat aatcattatc ttttgttttc tggccaaaaa   1740
tgctgcccat ttatttctat ccctaattag tcaaactttc taataaatgt atttaacgtt   1800
aatgatgttt atttgcttgt tgtatactaa aaccattagt ttctataatt taaatgtcac   1860
ctaatatgag tgaaaatgtg tcagaggctg gggaagaatg tggatggaga aagggaaggt   1920
gttgatcaaa aagtacccaa gtttcagtta cacaggaggc atgagattga tctagtgcaa   1980
aaaatgatga gtataataaa taataatgca ctgtatattt tgaaattgct aaaagtagat   2040
ttaaaattga tttacataat attttacata tttataaagc acatgcaata tgttgttaca   2100
tgtatagaat gtgcaacgat caagtcaggg tatctgtggt atccaccact ttgagcattt   2160
atcgattcta tatgtcagga acatttcaag ttatctgttc tagcaaggaa atataaaata   2220
cattatagtt aactatggcc tatctacagt gcaactaaac actagatttt attcctttcc   2280
aactgtgggt ttgtattcat ttaccaccct cttttcattc cctttctcac ccacacactg   2340
tgccgggcct caggcatata ctattctact gtctgtctct gtaaggatta tcattttagc   2400
ttccacatat gagagaatgc atgcaaagtt tttctttcca tgtctggctt atttcactta   2460
acaaaatgac ctccgcttcc atccatgtta tttatattac ccaatagtgt tcataaatat   2520
atatacacac atatatacca cattgcattt gtccaattat tcattgacgg aaactggtta   2580
atgttatatc gttgctattg tgaatagtgc tgcaataaac acgcaagtgg ggatataatt   2640
tgaagagttt ttttgttgat gttccataca aattttaaga ttgttttgtc tatgtttgtg   2700
aaaatggcgt tagtattttc atagagattg cattgaatct gtagattgct ttgggtaagt   2760
atggttattt tgatggtatt aattttttca ttccatgaag atgagatgtc tttccatttg   2820
tttgtgtcct ctacattttc tttcatcaaa gttttgttgt attttgaag tagatgtatt   2880
```

-continued

```
tcaccttata gatcaagtgt attccctaaa tattttattt ttgtagctat tgtagatgaa   2940
attgccttct cgatttcttt ttcacttaat tcattattag tgtatggaaa tgttatggat   3000
ttttatttgt tggtttttaa tcaaaaactg tattaaactt agagttttt gtggagtttt    3060 taagttttc tagatataag atcatgacat ctaccaaaaa a                        3101
```

<210> SEQ ID NO 98
<211> LENGTH: 90
<212> TYPE: PRT
<213> ORGANISM: Homo sapien

<400> SEQUENCE: 98

```
Met Lys Phe Leu Ala Val Leu Val Leu Leu Gly Val Ser Ile Phe Leu
 1               5                  10                  15

Val Ser Ala Gln Asn Pro Thr Thr Ala Ala Pro Ala Asp Thr Tyr Pro
                20                  25                  30

Ala Thr Gly Pro Ala Asp Asp Glu Ala Pro Asp Ala Glu Thr Thr Ala
            35                  40                  45

Ala Ala Thr Thr Ala Thr Thr Ala Ala Pro Thr Thr Ala Thr Thr Ala
        50                  55                  60

Ala Ser Thr Thr Ala Arg Lys Asp Ile Pro Val Leu Pro Lys Trp Val
65                  70                  75                  80

Gly Asp Leu Pro Asn Gly Arg Val Cys Pro
                85                  90
```

<210> SEQ ID NO 99
<211> LENGTH: 197
<212> TYPE: PRT
<213> ORGANISM: Homo sapien

<400> SEQUENCE: 99

```
Met Ala Lys Asn Gly Leu Val Ile Cys Ile Leu Val Ile Thr Leu Leu
 1               5                  10                  15

Leu Asp Gln Thr Thr Ser His Thr Ser Arg Leu Lys Ala Arg Lys His
                20                  25                  30

Ser Lys Arg Arg Val Arg Asp Lys Asp Gly Asp Leu Lys Thr Gln Ile
            35                  40                  45

Glu Lys Leu Trp Thr Glu Val Asn Ala Leu Lys Glu Ile Gln Ala Leu
        50                  55                  60

Gln Thr Val Cys Leu Arg Gly Thr Lys Val His Lys Cys Tyr Leu
65                  70                  75                  80

Ala Ser Glu Gly Leu Lys His Phe His Glu Ala Asn Glu Asp Cys Ile
                85                  90                  95

Ser Lys Gly Gly Ile Leu Val Ile Pro Arg Asn Ser Asp Glu Ile Asn
            100                 105                 110

Ala Leu Gln Asp Tyr Gly Lys Arg Ser Leu Pro Gly Val Asn Asp Phe
        115                 120                 125

Trp Leu Gly Ile Asn Asp Met Val Thr Glu Gly Lys Phe Val Asp Val
    130                 135                 140

Asn Gly Ile Ala Ile Ser Phe Leu Asn Trp Asp Arg Ala Gln Pro Asn
145                 150                 155                 160

Gly Gly Lys Arg Glu Asn Cys Val Leu Phe Ser Gln Ser Ala Gln Gly
                165                 170                 175

Lys Trp Ser Asp Glu Ala Cys Arg Ser Ser Lys Arg Tyr Ile Cys Glu
            180                 185                 190
```

Phe Thr Ile Pro Gln
      195

<210> SEQ ID NO 100
<211> LENGTH: 3410
<212> TYPE: DNA
<213> ORGANISM: Homo sapien

<400> SEQUENCE: 100

| | | | | |
|---|---|---|---|---|
| gggaaccagc | ctgcacgcgc | tggctccggg | tgacagccgc | gcgcctcggc caggatctga | 60 |
| gtgatgagac | gtgtccccac | tgaggtgccc | cacagcagca | ggtgttgagc atgggctgag | 120 |
| aagctggacc | ggcaccaaag | ggctggcaga | atgggcgcc | tggctgattc ctaggcagtt | 180 |
| ggcggcagca | aggaggagag | gccgcagctt | ctggagcaga | gccgagacga agcagttctg | 240 |
| gagtgcctga | acggcccct | gagccctacc | cgcctggccc | actatggtcc agaggctgtg | 300 |
| ggtgagccgc | ctgctgcggc | accggaaagc | ccagctcttg | ctggtcaacc tgctaacctt | 360 |
| tggcctggag | gtgtgtttgg | ccgcaggcat | cacctatgtg | ccgcctctgc tgctggaagt | 420 |
| gggggtagag | gagaagttca | tgaccatggt | gctgggcatt | ggtccagtgc tgggcctggt | 480 |
| ctgtgtcccg | ctcctaggct | cagccagtga | ccactggcgt | ggacgctatg ccgccgccg | 540 |
| gcccttcatc | tgggcactgt | ccttgggcat | cctgctgagc | ctctttctca tcccaagggc | 600 |
| cggctggcta | gcagggctgc | tgtgcccgga | tcccaggccc | ctggagctgg cactgctcat | 660 |
| cctgggcgtg | gggctgctgg | acttctgtgg | ccaggtgtgc | ttcactccac tggaggccct | 720 |
| gctctctgac | ctcttccggg | acccggacca | ctgtcgccag | gcctactctg tctatgcctt | 780 |
| catgatcagt | cttggggct | gcctgggcta | cctcctgcct | gccattgact gggacaccag | 840 |
| tgccctggcc | ccctacctgg | gcacccagga | ggagtgcctc | tttggcctgc tcaccctcat | 900 |
| cttcctcacc | tgcgtagcag | ccacactgct | ggtggctgag | gaggcagcgc tgggccccac | 960 |
| cgagccagca | gaagggctgt | cggcccctc | cttgtcgccc | cactgctgtc catgccgggc | 1020 |
| ccgcttggct | ttccggaacc | tgggcgccct | gcttccccgg | ctgcaccagc tgtgctgccg | 1080 |
| catgccccgc | accctgcgcc | ggctcttcgt | ggctgagctg | tgcagctgga tggcactcat | 1140 |
| gaccttcacg | ctgtttttaca | cggatttcgt | gggcgagggg | ctgtaccagg gcgtgcccag | 1200 |
| agctgagccg | ggcaccgagg | cccggagaca | ctatgatgaa | ggcgttcgga tgggcagcct | 1260 |
| ggggctgttc | ctgcagtgcg | ccatctccct | ggtcttctct | ctggtcatgg accggctggt | 1320 |
| gcagcgattc | ggcactcgag | cagtctattt | ggccagtgtg | gcagctttcc ctgtggctgc | 1380 |
| cggtgccaca | tgcctgtccc | acagtgtggc | cgtggtgaca | gcttcagccg ccctcaccgg | 1440 |
| gttcaccttc | tcagccctgc | agatcctgcc | ctacacactg | gcctccctct accaccggga | 1500 |
| gaagcaggtg | ttcctgccca | ataccgagg | ggacactgga | ggtgctagca gtgaggacag | 1560 |
| cctgatgacc | agcttcctgc | caggccctaa | gcctggagct | cccttcccta atggacacgt | 1620 |
| gggtgctgga | ggcagtggcc | tgctcccacc | tccacccgcg | ctctgcgggg cctctgcctg | 1680 |
| tgatgtctcc | gtacgtgtgg | tggtgggtga | gcccaccgag | gccagggtgg ttccgggccg | 1740 |
| ggcatctgc | ctggacctcg | ccatcctgga | tagtgccttc | ctgctgtccc aggtggcccc | 1800 |
| atccctgttt | atgggctcca | ttgtccagct | cagccagtct | gtcactgcct atatggtgtc | 1860 |
| tgccgcaggc | ctgggtctgg | tcgccatttta | ctttgctaca | caggtagtat ttgacaagag | 1920 |
| cgacttggca | aaatactcag | cgtagaaaac | ttccagcaca | ttggggtgga gggcctgcct | 1980 |
| cactgggtcc | cagctccccg | ctcctgttag | ccccatgggg | ctgccgggct ggccgccagt | 2040 |

-continued

```
ttctgttgct gccaaagtaa tgtgctctc tgctgccacc ctgtgctgct gaggtgcgta    2100
gctgcacagc tgggggctgg ggcgtccctc tcctctctcc ccagtctcta gggctgcctg    2160
actggaggcc ttccaagggg gtttcagtct ggacttatac agggaggcca gaagggctcc    2220
atgcactgga atgcgggac tctgcaggtg gattacccag gctcagggtt aacagctagc     2280
ctcctagttg agacacacct agagaagggt ttttgggagc tgaataaact cagtcacctg    2340
gtttcccatc tctaagcccc ttaacctgca gcttcgttta atgtagctct tgcatgggag    2400
tttctaggat gaaacactcc tccatgggat ttgaacatat gacttatttg taggggaaga    2460
gtcctgaggg gcaacacaca agaaccaggt cccctcagcc cacagcactg tcttttttgct   2520
gatccacccc cctcttacct tttatcagga tgtggcctgt tggtccttct gttgccatca    2580
cagagacaca ggcatttaaa tatttaactt atttatttaa caaagtagaa gggaatccat    2640
tgctagcttt tctgtgttgg tgtctaatat ttgggtaggg tgggggatcc ccaacaatca    2700
ggtcccctga gatagctggt cattgggctg atcattgcca gaatcttctt ctcctggggt    2760
ctggcccccc aaaatgccta acccaggacc ttggaaattc tactcatccc aaatgataat    2820
tccaaatgct gttacccaag gttagggtgt tgaaggaagg tagagggtgg ggcttcaggt    2880
ctcaacggct tccctaacca cccctcttct cttggcccag cctggttccc cccacttcca    2940
ctcccctcta ctctctctag gactgggctg atgaaggcac tgcccaaaat ttcccctacc    3000
cccaactttc ccctaccccc aactttcccc accagctcca caaccctgtt tggagctact    3060
gcaggaccag aagcacaaag tgcggtttcc caagcctttg tccatctcag cccccagagt    3120
atatctgtgc ttggggaatc tcacacagaa actcaggagc accccctgcc tgagctaagg    3180
gaggtcttat ctctcagggg gggtttaagt gccgtttgca ataatgtcgt cttatttatt    3240
tagcggggtg aatattttat actgtaagtg agcaatcaga gtataatgtt tatggtgaca    3300
aaattaaagg ctttcttata tgtttaaaaa aaaaaaaaa aaaaaaaaaa aaaaaaaaa      3360
aaaaaaaara aaaaaaaaa aaaaaaaaa aaaaaataa aaaaaaaaa                   3410
```

<210> SEQ ID NO 101
<211> LENGTH: 553
<212> TYPE: PRT
<213> ORGANISM: Homo sapien

<400> SEQUENCE: 101

```
Met Val Gln Arg Leu Trp Val Ser Arg Leu Leu Arg His Arg Lys Ala
 1               5                  10                  15

Gln Leu Leu Val Asn Leu Leu Thr Phe Gly Leu Glu Val Cys Leu
            20                  25                  30

Ala Ala Gly Ile Thr Tyr Val Pro Pro Leu Leu Glu Val Gly Val
        35                  40                  45

Glu Glu Lys Phe Met Thr Met Val Leu Gly Ile Gly Pro Val Leu Gly
 50                  55                  60

Leu Val Cys Val Pro Leu Leu Gly Ser Ala Ser Asp His Trp Arg Gly
 65                  70                  75                  80

Arg Tyr Gly Arg Arg Pro Phe Ile Trp Ala Leu Ser Leu Gly Ile
            85                  90                  95

Leu Leu Ser Leu Phe Leu Ile Pro Arg Ala Gly Trp Leu Ala Gly Leu
                100                 105                 110

Leu Cys Pro Asp Pro Arg Pro Leu Glu Leu Ala Leu Ile Leu Gly
            115                 120                 125

Val Gly Leu Leu Asp Phe Cys Gly Gln Val Cys Phe Thr Pro Leu Glu
```

```
        130                 135                 140
Ala Leu Leu Ser Asp Leu Phe Arg Asp Pro Asp His Cys Arg Gln Ala
145                 150                 155                 160
Tyr Ser Val Tyr Ala Phe Met Ile Ser Leu Gly Gly Cys Leu Gly Tyr
                165                 170                 175
Leu Leu Pro Ala Ile Asp Trp Asp Thr Ser Ala Leu Ala Pro Tyr Leu
            180                 185                 190
Gly Thr Gln Glu Glu Cys Leu Phe Gly Leu Leu Thr Leu Ile Phe Leu
        195                 200                 205
Thr Cys Val Ala Ala Thr Leu Leu Val Ala Glu Ala Ala Leu Gly
    210                 215                 220
Pro Thr Glu Pro Ala Glu Gly Leu Ser Ala Pro Ser Leu Ser Pro His
225                 230                 235                 240
Cys Cys Pro Cys Arg Ala Arg Leu Ala Phe Arg Asn Leu Gly Ala Leu
                245                 250                 255
Leu Pro Arg Leu His Gln Leu Cys Cys Arg Met Pro Arg Thr Leu Arg
            260                 265                 270
Arg Leu Phe Val Ala Glu Leu Cys Ser Trp Met Ala Leu Met Thr Phe
        275                 280                 285
Thr Leu Phe Tyr Thr Asp Phe Val Gly Glu Gly Leu Tyr Gln Gly Val
    290                 295                 300
Pro Arg Ala Glu Pro Gly Thr Glu Ala Arg Arg His Tyr Asp Glu Gly
305                 310                 315                 320
Val Arg Met Gly Ser Leu Gly Leu Phe Leu Gln Cys Ala Ile Ser Leu
                325                 330                 335
Val Phe Ser Leu Val Met Asp Arg Leu Val Gln Arg Phe Gly Thr Arg
            340                 345                 350
Ala Val Tyr Leu Ala Ser Val Ala Ala Phe Pro Val Ala Ala Gly Ala
        355                 360                 365
Thr Cys Leu Ser His Ser Val Ala Val Val Thr Ala Ser Ala Ala Leu
    370                 375                 380
Thr Gly Phe Thr Phe Ser Ala Leu Gln Ile Leu Pro Tyr Thr Leu Ala
385                 390                 395                 400
Ser Leu Tyr His Arg Glu Lys Gln Val Phe Leu Pro Lys Tyr Arg Gly
                405                 410                 415
Asp Thr Gly Gly Ala Ser Ser Glu Asp Ser Leu Met Thr Ser Phe Leu
            420                 425                 430
Pro Gly Pro Lys Pro Gly Ala Pro Phe Pro Asn Gly His Val Gly Ala
        435                 440                 445
Gly Gly Ser Gly Leu Leu Pro Pro Pro Ala Leu Cys Gly Ala Ser
    450                 455                 460
Ala Cys Asp Val Ser Val Arg Val Val Gly Glu Pro Thr Glu Ala
465                 470                 475                 480
Arg Val Val Pro Gly Arg Gly Ile Cys Leu Asp Leu Ala Ile Leu Asp
                485                 490                 495
Ser Ala Phe Leu Leu Ser Gln Val Ala Pro Ser Leu Phe Met Gly Ser
            500                 505                 510
Ile Val Gln Leu Ser Gln Ser Val Thr Ala Tyr Met Val Ser Ala Ala
        515                 520                 525
Gly Leu Gly Leu Val Ala Ile Tyr Phe Ala Thr Gln Val Val Phe Asp
    530                 535                 540
Lys Ser Asp Leu Ala Lys Tyr Ser Ala
545                 550
```

<210> SEQ ID NO 102
<211> LENGTH: 940
<212> TYPE: DNA
<213> ORGANISM: Human

<400> SEQUENCE: 102

| | | | | | |
|---|---|---|---|---|---|
| tttactgctt | ggcaaagtac | cctgagcatc | agcagagatg | ccgagatgaa | atcagggaac | 60 |
| tcctagggga | tgggtcttct | attacctggg | aacacctgag | ccagatgcct | tacaccacga | 120 |
| tgtgcatcaa | ggaatgcctc | cgcctctacg | caccggtagt | aaacatatcc | cggttactcg | 180 |
| acaaacccat | cacctttcca | gatggacgct | ccttacctgc | aggaataact | gtgtttatca | 240 |
| atatttgggc | tcttcaccac | aacccctatt | tctgggaaga | ccctcaggtc | tttaacccct | 300 |
| tgagattctc | cagggaaaat | tctgaaaaaa | tacatcccta | tgccttcata | ccattctcag | 360 |
| ctggattaag | gaactgcatt | gggcagcatt | ttgccataat | tgagtgtaaa | gtggcagtgg | 420 |
| cattaactct | gctccgcttc | aagctggctc | cagaccactc | aaggcctccc | cagcctgttc | 480 |
| gtcaagttgt | cctcaagtcc | aagaatggaa | tccatgtgtt | tgcaaaaaaa | gtttgctaat | 540 |
| tttaagtcct | ttcgtataag | aattaatgag | acaattttcc | taccaaagga | agaacaaaag | 600 |
| gataaatata | atacaaaata | tatgtatatg | gttgtttgac | aaattatata | acttaggata | 660 |
| cttctgactg | gttttgacat | ccattaacag | taattttaat | ttctttgctg | tatctggtga | 720 |
| aacccacaaa | aacmcctgaa | aaaactcaag | ctgacttcca | ctgcgaaggg | aaattattgg | 780 |
| tttgtgtaac | tagtggtaga | gtggctttca | agcatagttt | gatcaaaact | ccactcagta | 840 |
| tctgcattac | ttttatytyt | gcaaatatct | gcatgatagc | tttattytca | gttatctttc | 900 |
| cccataataa | aaaatatctg | ccaaaaaaaa | aaaaaaaaa | | | 940 |

<210> SEQ ID NO 103
<211> LENGTH: 529
<212> TYPE: DNA
<213> ORGANISM: Human

<400> SEQUENCE: 103

| | | | | | |
|---|---|---|---|---|---|
| tttttttttt | tttttactga | tagatggaat | ttattaagct | tttcacatgt | gatagcacat | 60 |
| agttttaatt | gcatccaaag | tactaacaaa | aactctagca | atcaaraatg | gcagcatgtt | 120 |
| attttataac | aatcaacacc | tgtggctttt | aaaatttggt | tttcataara | taatttatac | 180 |
| tgaagtaaat | ctagccatgc | ttttaaaaaa | tgctttaggt | cactccaagc | ttggcagtta | 240 |
| acatttggca | taaacaataa | taaaacaatc | acaatttaat | aaataacaaa | tacaacattg | 300 |
| taggccataa | tcatatacag | tataaggaaa | aggkggtagt | gttgagtaag | cagttattag | 360 |
| aatagaatac | cttggcctct | atgcaaatat | gtctaracac | tttgattcac | tcagccctga | 420 |
| cattcagttt | tcaaagtagg | agacaggttc | tacagtatca | ttttacagtt | tccaacacat | 480 |
| tgaaaacaag | tagaaaatga | tgagttgatt | tttattaatg | cattacatc | | 529 |

<210> SEQ ID NO 104
<211> LENGTH: 469
<212> TYPE: DNA
<213> ORGANISM: Human

<400> SEQUENCE: 104

| | | | | | |
|---|---|---|---|---|---|
| cccaacacaa | tggataaaaa | cacttatagt | aaatggggac | attcactata | atgatctaag | 60 |
| aagctacaga | ttgtcatagt | tgttttcctg | ctttacaaaa | ttgctccaga | tctggaatgc | 120 |

```
cagtttgacc tttgtcttct ataatatttc ctttttttcc cctctttgaa tctctgtata      180
tttgattctt aactaaaatt gttctcttaa atattctgaa tcctggtaat taaaagtttg      240
ggtgtatttt ctttacctcc aaggaaagaa ctactagcta caaaaaatat tttggaataa      300
gcattgtttt ggtataaggt acatattttg gttgaagaca ccagactgaa gtaaacagct      360
gtgcatccaa tttattatag ttttgtaagt aacaatatgt aatcaaactt ctaggtgact      420
tgagagtgga acctcctata tcattattta gcaccgtttg tgacagtaa                 469

<210> SEQ ID NO 105
<211> LENGTH: 744
<212> TYPE: DNA
<213> ORGANISM: Human

<400> SEQUENCE: 105
ggcctgggac aggattgagg tatgttgcag cctccagggc ctggggtctc ctgcatgaag       60
ataccccctc cccatttgac tgtgaacttt ttggcctgga ttctggagaa cagatttcca      120
ggattgtcag ccagaaggca gacagatgca ggcacctacc aagacctgac ctcaggaagt      180
ggccctgccc tacagcccag ttgctcagcc agggctgaag gccatggggc cccagcaccc      240
ttgcttcagt gccagcccct ggaaggaacc tcacaacagg gatacagcaa ggacactcca      300
gttcccccag tcctgccatg gtgctaccct gagggacagg gatggagaca gggcagccag      360
gtttgccagg acctgcatag cgggcccaag actgcccttc ctcttaagtc atgccaaagc      420
ctccctgccc agtctgagac agtcgctggc aggtgaccac gacctgcgtg ccctcccgg       480 cagttgtcat ggtggttgta ccccacccca tcccccctgag gagacatggg ctcagtccca      540
tgcctggtgc ccacagccac aaagatggcc atgggtctct agcctgatat tcgtggcctg      600 gcagggtca gcacccctga gggcatccaa gccatggtca gaggaaagtg ttggcaggct      660
cggcacagcc aaagaagtca ggacccacga gacgggggaa gccttccaga gccttcacct      720
tcacagggtc aaacttccag taga                                            744

<210> SEQ ID NO 106
<211> LENGTH: 401
<212> TYPE: DNA
<213> ORGANISM: Human

<400> SEQUENCE: 106
acattgttag gtgctgacct agacagagat gaactgaggt ccttgttttg ttttgttcat       60
aatacaaagg tgctaattaa tagtatttca gatacttgaa gaatgttgat ggtgctagaa      120
gaatttgaga agaaatactc ctgtattgag ttgtatcgtg tggtgtattt tttaaaaaat      180
ttgatttagc attcatattt tccatcttat tcccaattaa agtatgcag attatttgcc      240 caaatcttct tcagattcag catttgttct ttgccagtct cattttcatc ttcttccatg      300
gttccacaga agctttgttt cttgggcaag cagaaaaatt aaattgtacc tattttgtat      360
atgtgagatg tttaaataaa ttgtgaaaaa atgaaaataa a                         401

<210> SEQ ID NO 107
<211> LENGTH: 1009
<212> TYPE: DNA
<213> ORGANISM: Human

<400> SEQUENCE: 107
cgagctatta tggtacggaa ctttttttaa tgaggaattt catgatgatt taggaatttt       60
ctctcttgga aaaggcttcc cctgtgatga aaatgatgtg ccagctaaaa ttgtgtgcca      120
```

```
tttaaaaact gaaaatattt taaaattatt tgtctatatt ctaaattgag ctttggatca        180
aactttaggc caggaccagc tcatgcgttc tcattcttcc ttttctcact ctttctctca        240
tcactcacct ctgtattcat tctgttgttt gggatagaaa aatcataaag agccaaccca        300
tctcagaacg ttgtggattg agagagacac tacatgactc caagtatatg agaaaaggac        360
agagctctaa ttgataactc tgtagttcaa aaggaaaaga gtatgcccaa ttctctctac        420
atgacatatt gagatttttt ttaatcaact tttaagatag tgatgttctg ttctaaactg        480
ttctgtttta gtgaaggtag atttttataa aacaagcatg gggattcttt tctaaggtaa        540
tattaatgag aagggaaaaa agtatcttta acagctcttt gttgaagcct gtggtagcmc        600
attatgttta taattgcaca tgtgcacata atctattatg atccaatgca aatacagctc        660
caaaaatatt aaatgtatat atattttaaa atgcctgagg aaatacattt ttcttaataa        720
actgaagagt ctcagtatgg ctattaaaat aattattagc ctcctgttgt gtggctgcaa        780
aacatcacaa agtgaccggt cttgagacct gtgaactgct gccctgttta gtaaataaaa        840
ttaatgcatt tctagagggg gaatatctgc catccagtgg tggaaatgtg gagtaaagaa        900
gctggtggtc tgcttctgtg ctgtatgcca gccttttgcc ttaagttgag aggaggtcaa        960
ctttagctac tgtctttggt ttgagagcca tggcaaaaaa aaaaaaaaa                   1009
```